(12) United States Patent
Devi et al.

(10) Patent No.: US 9,216,189 B2
(45) Date of Patent: Dec. 22, 2015

(54) ANTIBODIES WHICH BIND TYPE I CANNABINOID RECEPTOR/ANGIOTENSIS II RECEPTOR HETEROMERS

(75) Inventors: Lakshmi A. Devi, New Rochelle, NY (US); Raphael Rozenfeld, Swampscott, MA (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 557 days.

(21) Appl. No.: 13/575,220

(22) PCT Filed: Jan. 25, 2011

(86) PCT No.: PCT/US2011/022452
§ 371 (c)(1),
(2), (4) Date: Mar. 18, 2013

(87) PCT Pub. No.: WO2011/091435
PCT Pub. Date: Jul. 28, 2011

(65) Prior Publication Data
US 2013/0171145 A1 Jul. 4, 2013

Related U.S. Application Data

(60) Provisional application No. 61/297,895, filed on Jan. 25, 2010.

(51) Int. Cl.
| | |
|---|---|
| *A61K 39/395* | (2006.01) |
| *C07K 16/18* | (2006.01) |
| *C07K 16/28* | (2006.01) |
| *A61K 31/7076* | (2006.01) |
| *C07K 16/44* | (2006.01) |
| *A61K 31/454* | (2006.01) |

(52) U.S. Cl.
CPC ........... *A61K 31/7076* (2013.01); *A61K 31/454* (2013.01); *C07K 16/286* (2013.01); *C07K 16/2869* (2013.01); *C07K 16/44* (2013.01); *C07K 2317/32* (2013.01); *C07K 2317/76* (2013.01)

(58) Field of Classification Search
None
See application file for complete search history.

(56) References Cited

U.S. PATENT DOCUMENTS

| 6,855,807 B1 | 2/2005 | Devi et al. |
| 2009/0123477 A1 | 5/2009 | Hanke et al. |
| 2009/0247499 A1 | 10/2009 | Fletcher et al. |

OTHER PUBLICATIONS

Turu et al., "Paracrine Transactivation of the CB1 Cannabinoid Receptor by AT1 Angiotensin and Other Gq/11 Protein-coupled Receptors," J. Biol Chem, (2009), vol. 284, No. 25, pp. 16914-16921.
Turu et al., "The Role of Diacylglycerol Lipase in Constitutive and Angiotensin AT1 Receptorstimulated Cannabinoid CB1 Receptor Activity," J. Biol Chem, (2007), vol. 282, No. 11, pp. 7753-7757.
McIntosh et al., "Agonist-dependent cannabinoid receptor signalling in human trabecular meshwork cells," British Journal of Pharmacology (2007), vol. 152, No. 7, pp. 1111-1120.
International Search Report mailed Jul. 22, 2011, which issued in corresponding International Application Serial No. PCT/US2011/022452.

*Primary Examiner* — Christine J Saoud
*Assistant Examiner* — Jon M Lockard
(74) *Attorney, Agent, or Firm* — Fish & Richardson P.C.

(57) ABSTRACT

Compounds and compositions useful for the treatment of liver diseases and methods of treating liver diseases are disclosed. The compounds of the invention specifically interact with heteromers of cannabinoid receptors as compared to monomers or homodimers. The invention also relates to methods of screening for compounds useful for the treatment of liver diseases and to methods of screening for diacylglycerol lipase inhibitors.

2 Claims, 21 Drawing Sheets

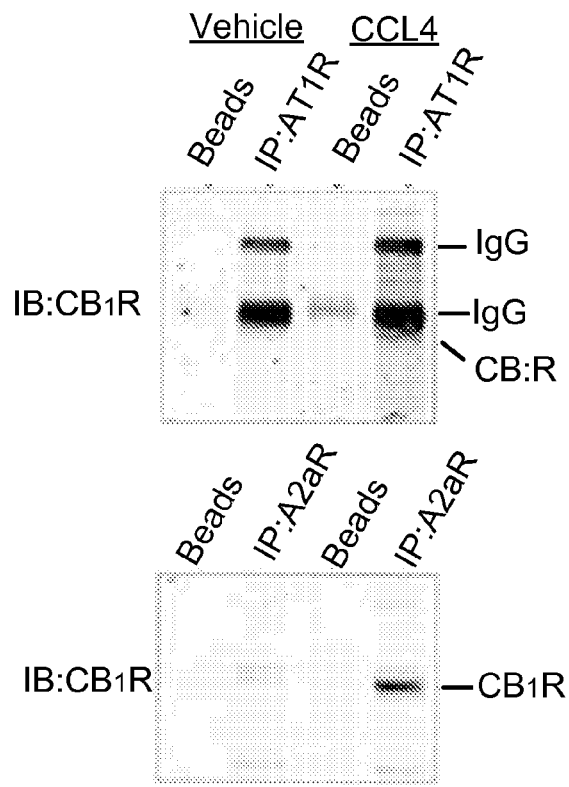
FIG. 1F
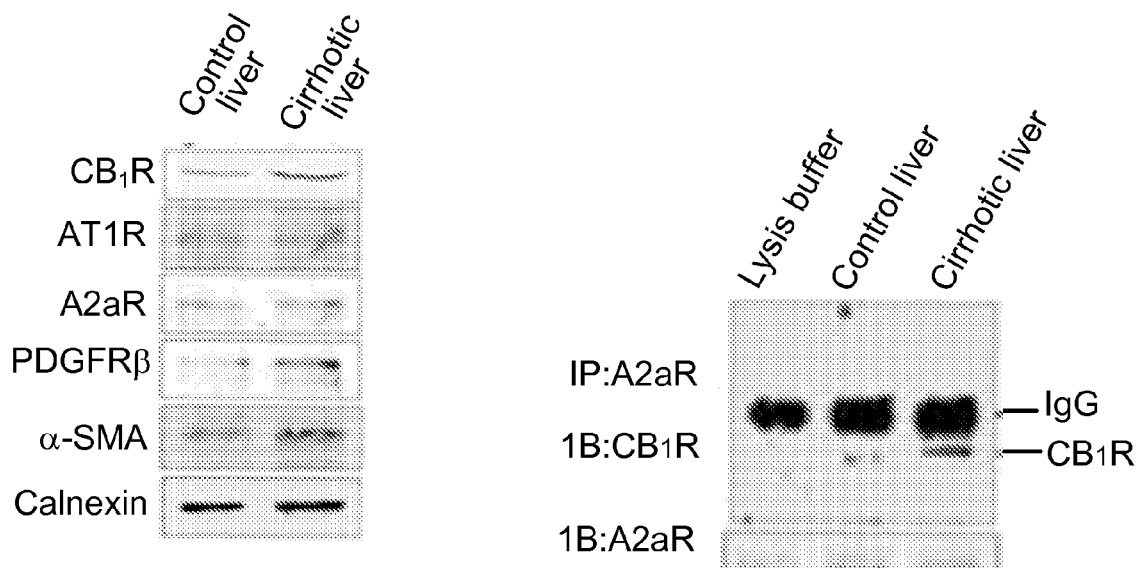
FIG. 1G
FIG. 1H

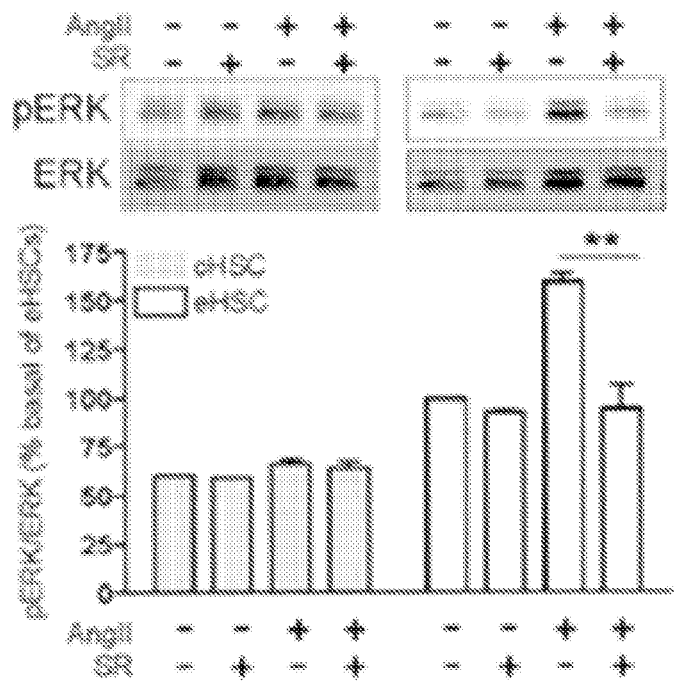
FIG. 2A
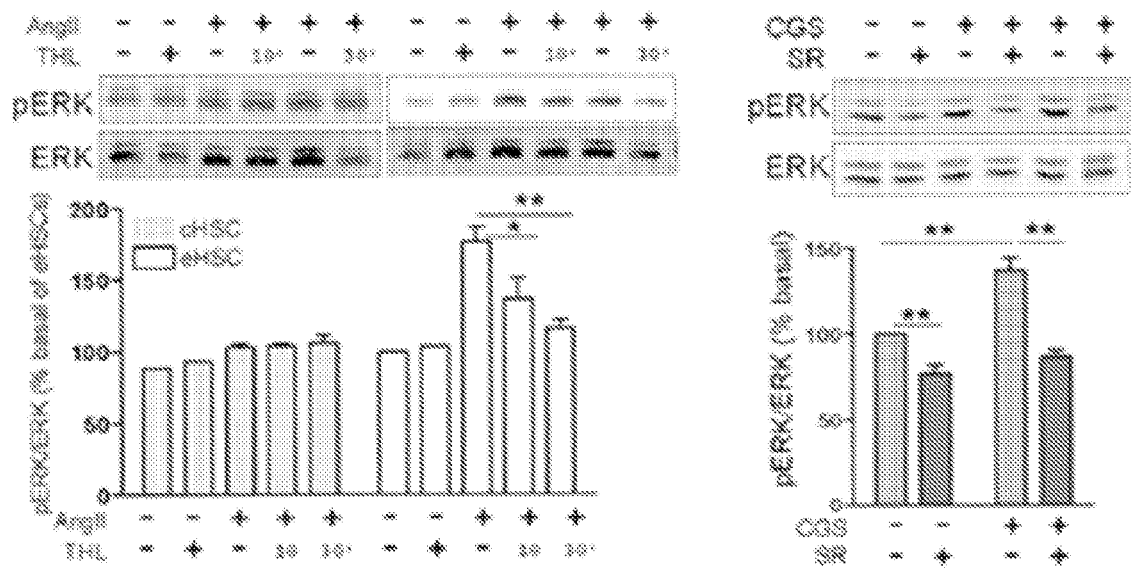
FIG. 2B
FIG. 2C

FIG. 8A
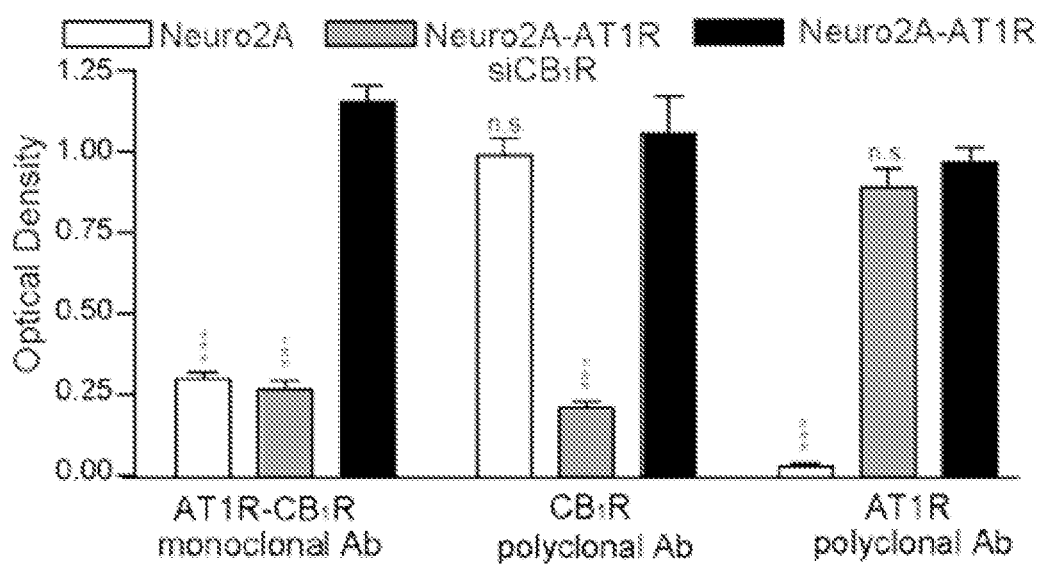
FIG. 8B

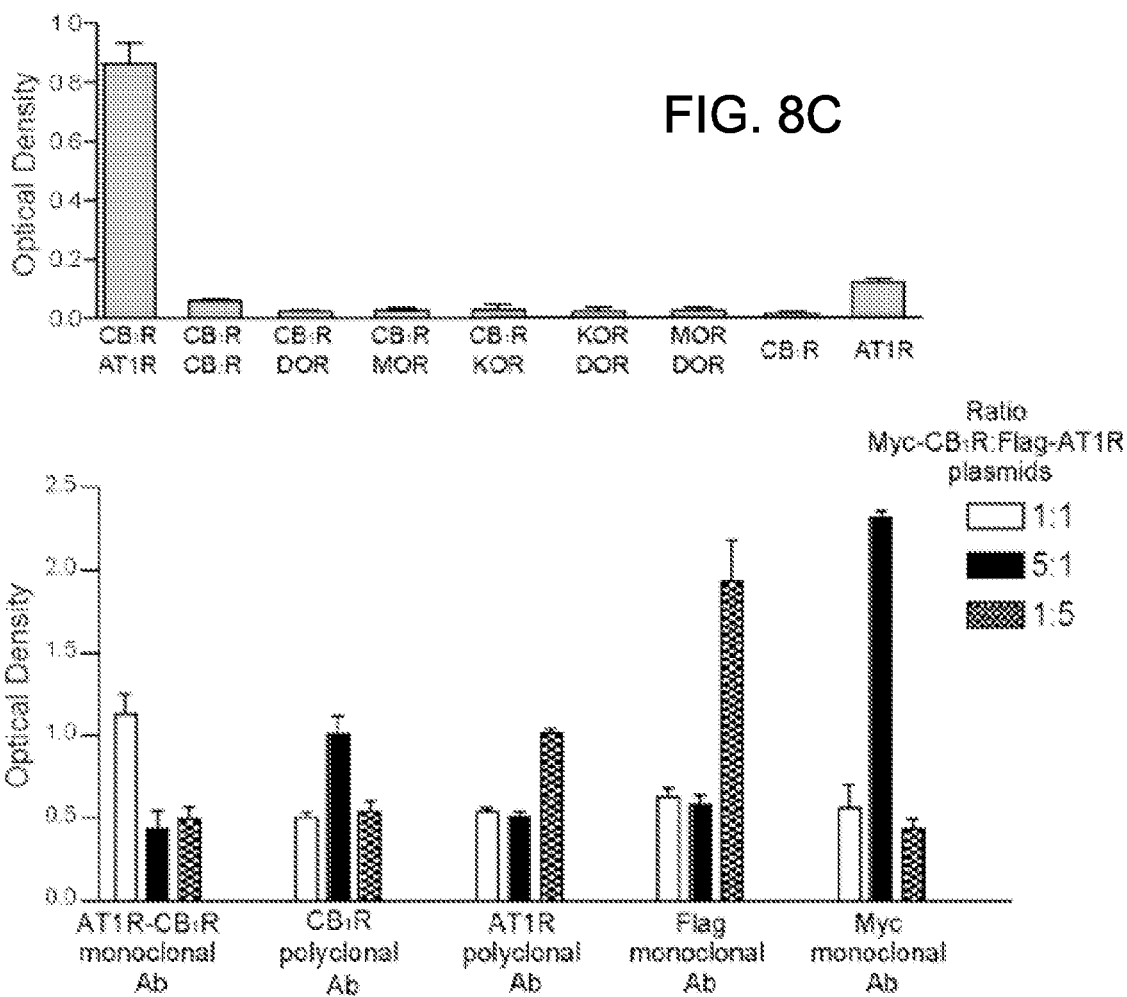
FIG. 8C
FIG. 8D
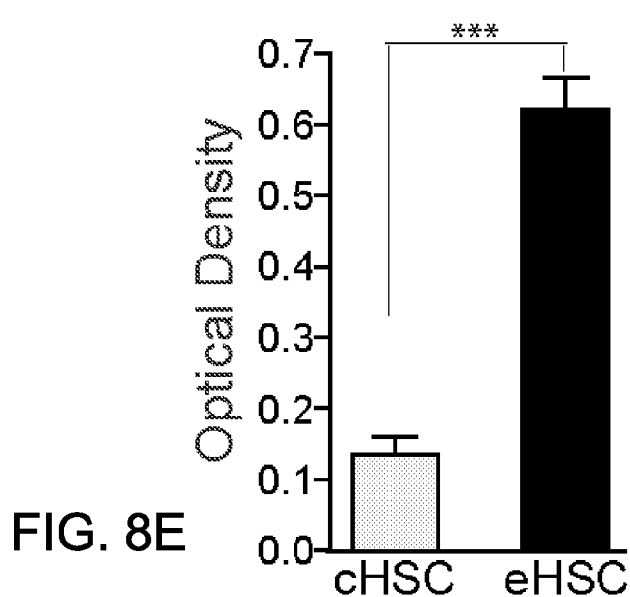
FIG. 8E

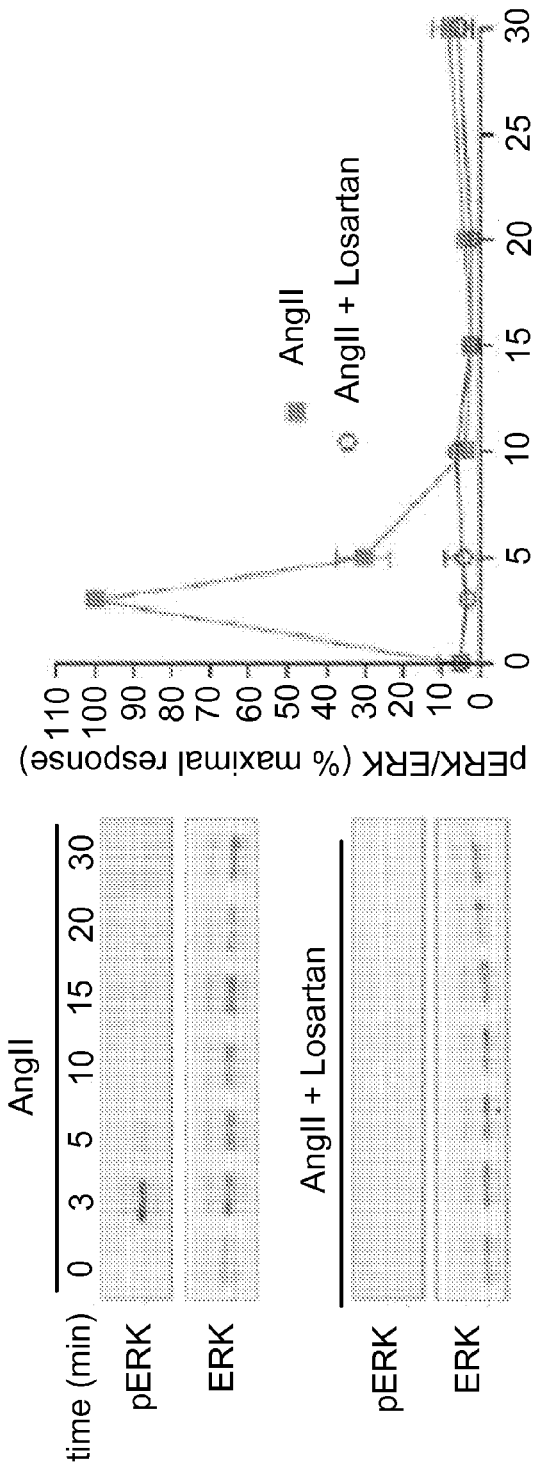
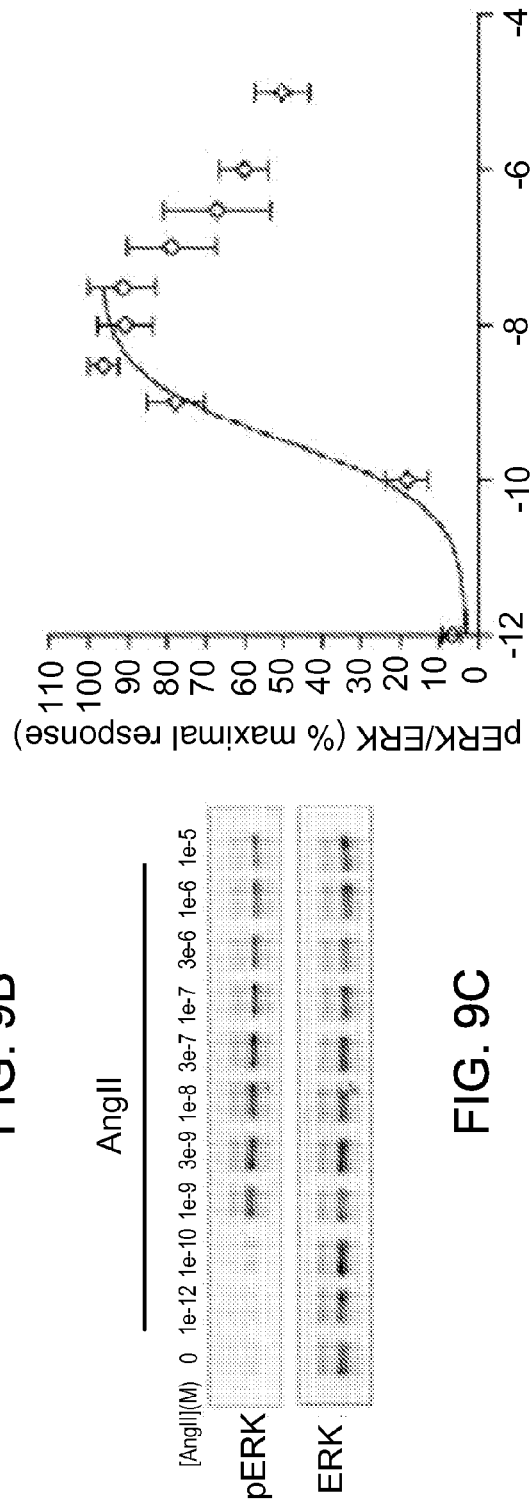
FIG. 9B
FIG. 9C

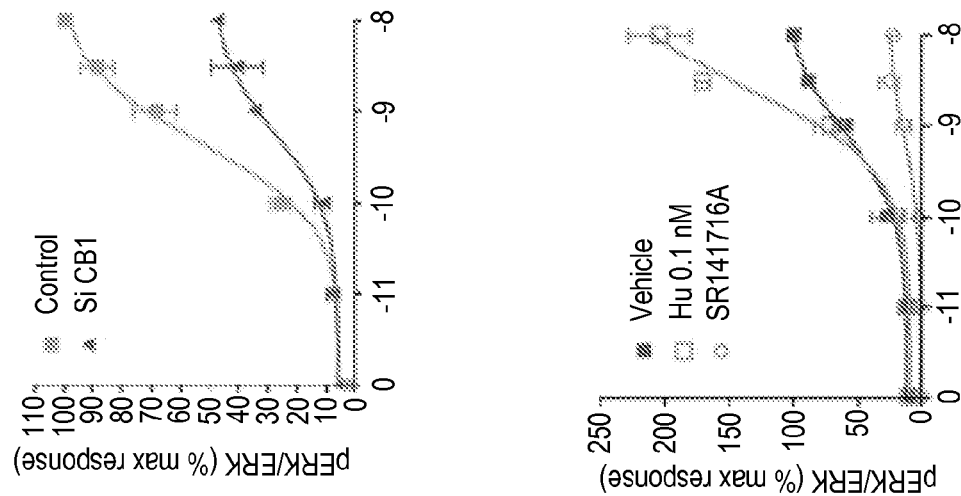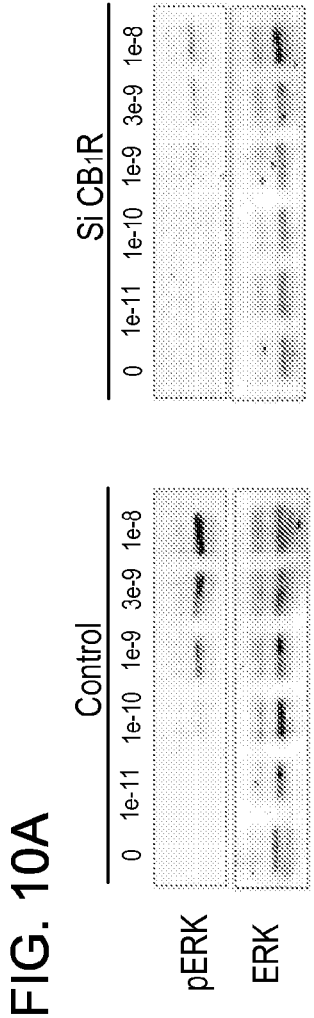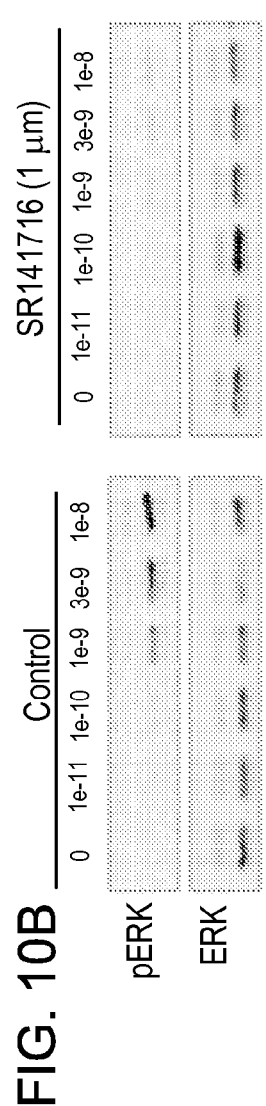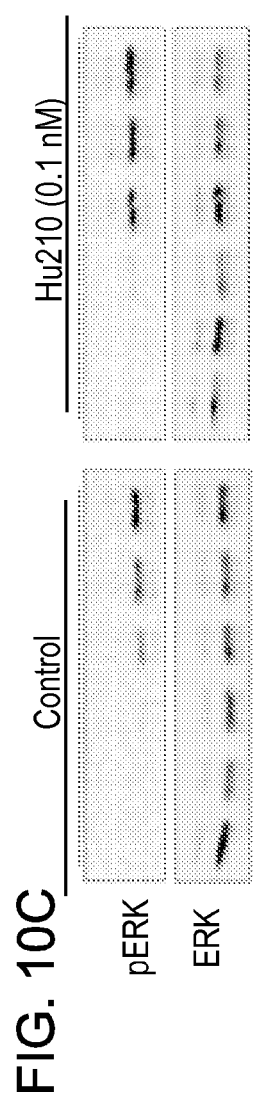
FIG. 10A
FIG. 10B
FIG. 10C

ANTIBODIES WHICH BIND TYPE I CANNABINOID RECEPTOR/ANGIOTENSIS II RECEPTOR HETEROMERS

CROSS REFERENCE TO PRIOR APPLICATIONS

This is a U.S. National Phase application under 35 U.S.C. §371 of International Patent Application No. PCT/US2011/022452, filed Jan. 25, 2011, and claims the benefit of U.S. provisional application No. 61/297,895, filed Jan. 25, 2010, both of which are incorporated by reference herein in their entirety. The International Application published in English on Jul. 28, 2011 as WO 2011/091435 under PCT Article 21(2).

GOVERNMENT SPONSORED RESEARCH OR DEVELOPMENT

This invention was made with support received from the National Institutes of Health, Department of Health and Human Services, under grant no. DA08863. The U.S. government has certain rights in the invention.

FIELD OF THE INVENTION

The present invention is related to compounds and compositions useful for the treatment of liver diseases and related screening and therapeutic methods. The present invention also relates to methods of screening for diacylglycerol lipase inhibitors.

BACKGROUND OF THE INVENTION

A fundamental question in liver biology is how type I cannabinoid receptors ($CB_1Rs$) mediate liver fibrosis. Cannabinoid receptors are a class of G-protein coupled receptors (GPCRs). Cannabinoid receptors exhibit marginal expression in the normal liver but undergo enhanced expression in the fibrotic human liver, predominately in activated hepatic stellate cells (HSCs)[2]. A critical aspect in chronic liver disease is the activation of resident HSCs into proliferative, contractile, and fibrogenic cells. These myofibroblasts produce an excess of extracellular matrix proteins including collagens, resulting in fibrosis. In these cells, specific mitogenic signaling cascades, upon activation of naturally occurring GPCRs such as AT1R and adenosine 2A receptor (A2aR) contribute to the fibrosis. HSCs are the cells primarily responsible for the fibrogenic response in the liver[1]. Preventing the expression or activation of $CB_1Rs$ attenuates the development of fibrosis[2]. $CB_1Rs$ contribute to fibrogenic response, since administration of the $CB_1R$ antagonist Rimonabant (SR141716) or genetic ablation of $CB_1R$ inhibits fibrosis progression in three distinct models of chronic liver injury (namely, $CCl_4$-, thioacetamide-, and bile duct ligation-induced fibrosis). However, the extent of the contribution of $CB_1Rs$ in alcohol-induced liver injury, and the molecular mechanism by which $CB_1Rs$ promote liver fibrosis are not understood.

Approximately 25,000 people die each year of cirrhosis in the United States. The leading causes of cirrhosis are viral hepatitis, alcoholism and obesity-related liver diseases. Close to 1 million people suffer from this disease, which is the 7th leading cause of death in the United States, and whose only effective treatment is liver transplantation. It is known that cannabinoid receptors are upregulated in the liver during liver fibrosis, and the blockade of the $CB_1$ subtype of the receptor has been shown to inhibit fibrogenesis, offering an approach for the treatment of cirrhosis. However, as $CB_1R$ expression is not localized specifically to the liver (in fact, $CB_1Rs$ are likely the most widely expressed GPCR in the brain), the treatment of liver fibrosis and cirrhosis by the administration of a $CB_1R$ inhibitor would like result in significant side effects. In fact, the targeting of $CB_1$ receptor in the treatment of obesity has posed serious safety problems associated with severe side effects. For example, (1) the Sanofi-Aventis $CB_1R$ antagonist Rimonabant (SR141716) was taken off the market because of its serious side effects; (2) Merck discontinued clinical trials with its $CB_1R$ inverse agonist Taranabant (MK-0364) due to the high level of central side effects, mainly depression and anxiety; and (3) Bristol Myers Squibb also discontinued development of its $CB_1R$ antagonist Otenabant (CP-945,598) following the problems seen during clinical use of the similar drug Rimonabant. Therefore, what are needed are specific antagonists that do not have these systemic, toxic side effects.

N-arachidonoyl-ethanolamine (AEA, anandamide) and 2-arachidonoyl glycerol (2-AG) are the two most studied endocannabinoids. They are biosynthesized by cleavage of their membrane lipid precursors N-arachidonoyl-phosphatidylethanolamine and sn-1-acyl-2-arachidonoylglycerols (DAGs) respectively, and then inactivated by intracellular hydrolyzing enzymes. The biological activity of AEA and 2-AG is mainly mediated by activation of the cannabinoid receptors $CB_1R$ and $CB_2R$.

2-AG has a variety of effects in vivo; it is a mediator of neurite outgrowth, during brain development, or as retrograde signal mediating depolarization-induced suppression of neurotransmission and synaptic plasticity, in the adult brain. It protects neurons from inflammation by preventing Cox2 gene expression (D2). In addition, 2-AG is involved in metabolic regulation and diseases. For example, it is involved in bone formation (D3), in obesity (its concentration is increased in several tissues and in the circulation of obese persons (D4)). 2-AG is highly upregulated during chronic liver diseases and is implicated in the pathogenesis of non-alcoholic fatty liver disease, progression of fibrosis to cirrhosis and the development of the cardiovascular abnormalities of cirrhosis, such as the hyperdynamic circulatory syndrome and cirrhotic cardiomiopathy (D5).

2-AG is produced from the hydrolysis of phosphoinositol bisphosphate (PIP2), catalyzed by the PIP2-selective phospholipase C, or from the hydrolysis of phosphatidic acid (PA), catalyzed by a PA phosphohydrolase into diacylglycerols (DAGs). DAGs are then converted into 2-AG by sn-1 selective-DAG lipases (DAGLs). Two sn-1 DAG lipase isozymes (DAGLα and DAGLβ) have been cloned and enzymatically characterized (D6). They are mostly located in the plasma membrane, are stimulated by $Ca^{2+}$ and glutathione, appear to possess a catalytic triad typical of serine hydrolases, and do not exhibit strong selectivity for 2-arachidonate-containing DAGs (FIG. 1). Endocannabinoids, including 2-AG, stimulate $CB_1R$, resulting, among other things, in the activation of the ERK1/2 pathway, and phosphorylation of ERK1/2.

Because AEA and 2-AG biosynthetic enzymes have been identified only recently, little information on the development of selective inhibitors for these proteins is currently available. RHC 80267 [1,6-bis-(cyclohexyloximino-carbonylamino)-hexane], and tetrahydrolipstatin (THL), have been shown to inhibit DAGL at concentrations lower than those required to inhibit other lipases (D6). Furthermore, two inhibitors of 2-AG biosynthesis have been developed so far, O-3640 and O-3841, with excellent selectivity for DAGLα over the other proteins of the endocannabinoid system tested. However, they are not suitable for in vivo use (D7). Therefore, the identification of new inhibitors of DAGLs, which could be used in vivo, is highly clinically relevant.

SUMMARY OF THE INVENTION

This Summary is provided to present a summary of the invention to briefly indicate the nature and substance of the invention. It is submitted with the understanding that it will not be used to interpret or limit the scope or meaning of the claims.

Embodiments of the invention comprise an isolated monoclonal antibody which specifically binds to a type I cannabinoid receptor ($CB_1R$)/angiotensin II receptor (AT1R) heteromer. In another preferred embodiment, a pharmaceutical composition comprises the monoclonal antibody and a pharmaceutically acceptable carrier or diluent.

In another preferred embodiment, a method of treating a liver disease in a mammal, comprises administering to the mammal in need of such treatment an effective amount of a compound, that preferentially inhibits an activity of a type I cannabinoid receptor ($CB_1R$)/angiotensin II receptor (AT1R) heteromer, as compared to a control receptor selected from the group consisting of $CB_1R$ monomer, $CB_1R$ homodimer, AT1R monomer, AT1R homodimer, and a combination thereof. Preferably, the activity of the $CB_1R$/AT1R heteromer is inhibited at least about 5-fold greater than the activity of the control receptor. Preferably the mammal is human.

In a preferred embodiment, the activity is determined by measuring phosphorylation of extracellular signal-regulated kinase-1 (ERK1) or extracellular signal-regulated kinase-2 (ERK2).

In another preferred embodiment, the liver disease is selected from the group consisting of liver fibrosis, a liver disease associated with obesity, a liver disease associated with metabolic syndrome, liver cirrhosis, alcoholic fibrosis, non-alcoholic fibrosis, fatty liver, hepatic cirrhosis, a diabetes-associated liver disease, genetic liver diseases, liver inflammation, liver steatosis, or chronic hepatitis.

In another preferred a method of treating a liver disease in a mammal, comprising administering to the mammal in need of such treatment an effective amount of a compound, that preferentially inhibits an activity of a type I cannabinoid receptor ($CB_1R$)/adenosine 2a receptor (A2aR) heteromer, as compared to a control receptor selected from the group consisting of $CB_1R$ monomer, $CB_1R$ homodimer, A2aR monomer, and A2aR homodimer. Preferably, the activity of $CB_1R$/A2aR heteromer is inhibited at least about 5-fold greater than the activity of the control receptor.

In another preferred embodiment, the activity is determined by measuring phosphorylation of extracellular signal-regulated kinase-1 (ERK1) or extracellular signal-regulated kinase-2 (ERK2).

In another preferred embodiment, a method of screening for a candidate compound useful for the treatment of a liver disease, the method comprises a) contacting the compound with a $CB_1R$/A2aR heteromer, and with at least one control receptor selected from the group consisting of a $CB_1R$ monomer, a $CB_1R$ homodimer, an A2aR monomer, and an A2aR homodimer, b) measuring inhibition of an activity of the $CB_1R$/A2aR heteromer and of the control receptor in the presence of the compound, and c) selecting the compound which preferentially inhibits the activity of the $CB_1R$/A2aR heteromer as compared to the control receptor, as a candidate compound useful for the treatment of the liver disease. Preferably, the wherein the candidate compound inhibits the activity of the $CB_1R$/A2aR heteromer at least about 5-fold greater than the activity of the control receptor.

In another preferred embodiment, the activity is determined by measuring phosphorylation of extracellular signal-regulated kinase-1 (ERK1) or extracellular signal-regulated kinase-2 (ERK2).

In another preferred embodiment, a method of screening for a compound useful for the treatment of a liver disease, the method comprises a) contacting the compound with a $CB_1R$/AT1R heteromer, and with at least one control receptor selected from the group consisting of a $CB_1R$ monomer, a $CB_1R$ homodimer, an AT1R monomer, and an AT1R homodimer; b) measuring inhibition of an activity of the $CB_1R$/AT1R heteromer and of the control receptor in the presence of the compound, and c) selecting the compound which preferentially inhibits the activity of the $CB_1R$/AT1R heteromer as compared to the control receptor, as a candidate compound useful for the treatment of the liver disease. Preferably, the candidate compound inhibits the activity of the $CB_1R$/AT1R heteromer at least about 5-fold greater than the activity of the control receptor. In one embodiment, the activity is determined by measuring phosphorylation of extracellular signal-regulated kinase-1 (ERK1) or extracellular signal-regulated kinase-2 (ERK2).

In another preferred embodiment, a method of screening for a compound useful for the treatment of a liver disease, the method comprises a) contacting the compound with a cell expressing a type I cannabinoid receptor ($CB_1R$)/angiotensin II receptor (AT1R) heteromer, and with a control cell expressing $CB_1R$ alone or AT1R alone; b) measuring inhibition of endocannabinoid activity in the cell expressing $CB_1R$/AT1R heteromer and in the control cell in the presence of the compound, and c) selecting the compound which preferentially inhibits endocannabinoid activity in the cell expressing the $CB_1R$/AT1R heteromer as compared to the control cell, as the candidate compound useful for the treatment of the liver disease.

In a preferred embodiment, the inhibition of endocannabinoid activity is determined by measuring angiotensin II-mediated ERK1/2 phosphorylation. Preferably, the inhibition of endocannabinoid activity in the cell expressing the $CB_1R$/AT1R heteromer is at least about 5-fold greater than the inhibition of endocannabinoid activity in the control cell. In one preferred embodiment, the cell expressing the $CB_1R$/AT1R heteromer, $CB_1R$ alone, or AT1R alone is HEK293 or CHO cell.

In another preferred embodiment, a method of screening for a compound useful for the treatment of a liver disease, the method comprises a) contacting the compound with a cell expressing a type I cannabinoid receptor ($CB_1R$)/adenosine 2a receptor (A2aR) heteromer, and with a control cell expressing $CB_1R$ alone or A2aR alone; b) measuring inhibition of endocannabinoid activity in the cell expressing $CB_1R$/A2aR heteromer and in the control cell in the presence of the compound, and c) selecting the compound which preferentially inhibits endocannabinoid activity in the cell expressing the $CB_1R$/A2aR heteromer as compared to the control cell, as the candidate compound useful for the treatment of the liver disease.

In one embodiment, the inhibition of endocannabinoid activity is determined by measuring adenosine-mediated ERK1/2 phosphorylation. Preferably, the inhibition of endocannabinoid activity in the cell expressing the $CB_1R$/A2aR heteromer is at least about 5-fold greater than the inhibition of endocannabinoid activity in the control cell. In another preferred embodiment, the cell expressing the $CB_1R$/A2aR heteromer, $CB_1R$ alone, or A2aR alone is HEK293 or CHO cell.

In another preferred embodiment, a method of screening for a compound useful for treating a liver disease, the method comprises a) contacting the compound with a cell expressing a type I cannabinoid receptor ($CB_1R$)/angiotensin II receptor (AT1R) heteromer, and with a control cell expressing $CB_1R$ alone or AT1R alone; b) measuring decrease in intracellular cAMP levels in the cell expressing $CB_1R$/AT1R heteromer and in the control cell in the presence of the compound, and c) selecting the compound which causes a greater decrease in intracellular cAMP levels in the cell expressing the $CB_1R$/AT1R heteromer as compared to the control cell, as the candidate compound useful for the treatment of the liver disease. In one embodiment, the intracellular cAMP levels are measured using a cAMP detection kit. Preferably, the decrease in intracellular cAMP levels in the cell expressing the $CB_1R$/AT1R heteromer is about at least 5 fold greater than the decrease in intracellular cAMP levels in the control cell.

In another preferred embodiment, a method of screening for a diacylglycerol lipase (DAGL) inhibitor, the method comprises a) contacting a compound with a cell expressing a type I cannabinoid receptor ($CB_1R$) and a G-protein coupled receptor (GPCR), each receptor having a respective ligand, wherein the receptors are only capable of inducing ERK1/2 phosphorylation when the $CB_1R$ and the GPCR are co-stimulated by a ligand, b) measuring changes in ERK1/2 phosphorylation in the presence of the compound, and c) selecting the compound which causes a decrease in ERK1/2 phosphorylation as the DAGL inhibitor.

In one embodiment, the GPCR is AT1R or A2aR.

In another preferred embodiment, the compound to be screened is pre-incubated with the CB1R and GPCR ligands and added to the cells. Preferably, the screen is a high-throughput screen.

In another preferred embodiment, a method of measuring selective binding of a compound to CB1R/AT1R or CB1R/A2aR heteromer, the method comprises a) providing a cell expressing CB1R/AT1R or CB1R/A2aR heteromer and a control cell expressing only CB1R, only AT1R, or only A2aR; b) contacting the cell expressing CB1R/AT1R or CB1R/A2aR heteromer and the control cell with Angiotensin II or A2aR agonist or the compound; c) adding a radioactive labeled Angiotensin II or A2aR agonist; and, d) measuring receptor-bound radioactivity. In one embodiment, the detection of the radiolabel is determinative of selective binding.

In another preferred embodiment, an isolated monoclonal antibody specifically binds to a type I cannabinoid receptor ($CB_1R$)/adenosine 2a receptor (A2aR) heteromer.

These and other aspects of the present invention will be apparent to those of ordinary skill in the art in light of the present specification, claims and drawings.

BRIEF DESCRIPTION OF THE DRAWINGS

FIGS. 1A-1H: Isolation of $CB_1R$/AT1R and $CB_1R$/A2aR complexes in activated hepatic stellate cells (HSCs) and fibrotic livers. Lysates were subjected to SDS-PAGE and immunoblotting. The levels of Ang II-mediated pERK normalized to total ERK were measured by Western blot. Data are expressed as the mean±SD (n=3-4).

FIG. 1A. Comparison of the expression levels of $CB_1R$, AT1R, and α-SMA. Western blot in HSCs from control (cHSC) and ethanol (eHSCs) treated rats.

FIG. 1B. Association of AT1R and $CB_1R$ in eHSCs. Lysates from cHSCs and eHSCs were subjected to immunoprecipitation using an anti-AT1R antibody/protein A/C agarose complex, and to Western blotting. $CB_1R$ is detected in the AT1R-immunoprecipitate from eHSCs.

FIG. 1C. Comparison of the expression levels of A2aR by Western blot in HSCs from control (cHSC) and ethanol (eHSCs) treated rats.

FIG. 1D. Association of A2aR and $CB_1R$ in eHSCs. Lysates from cHSCs and eHSCs were subjected to immunoprecipitation using an anti-A2aR antibody/protein A/C agarose complex, and to Western blotting. $CB_1R$ is detected in the A2aR immunoprecipitate from eHSCs.

FIG. 1E. Comparison of the expression levels of $CB_1R$, AT1R, A2aR and PDGFRβ by Western blot in livers from vehicle and $CCl_4$ treated mice.

FIG. 1F. Association of AT1R or A2aR with $CB_1R$ in mouse fibrotic livers. Lysates from the liver of vehicle or $CCl_4$ treated mice were subjected to immunoprecipitation using an anti-AT1R or an anti-A2aR antibody/protein A/C agarose complex, and to Western blotting. $CB_1R$ is detected in the AT1R and A2aR immunoprecipitates from livers from $CCl_4$ treated mice.

FIG. 1G. Comparison of the expression levels of $CB_1R$, AT1R, A2aR, PDGFRβ and α-SMA by Western blot in livers from control and cirrhotic human patients.

FIG. 1H. Association of A2aR and $CB_1R$ cirrhotic human livers. Lysates from control and cirrhotic human livers were subjected to immunoprecipitation using an anti-A2aR antibody/protein A/C agarose complex, and to Western blotting. $CB_1R$ is detected in the A2aR immunoprecipitate from eHSCs, and there is enhanced association in livers from cirrhotic patients as compared to control patients.

FIGS. 2A-2C: $CB_1R$ activity controls AT1R and A2aR signaling in activated HSCs.

FIG. 2A. $CB_1R$ antagonist prevents Ang II-mediated pERK in eHSCs. cHSCs and eHSCs were stimulated with Ang II in the absence or presence of SR141716 (SR).

FIG. 2B. Blocking the production of endocannabinoids reduces Ang II-mediated pERK. cHSCs and eHSCs pretreated with THL for 10 or 30 minutes were stimulated with Ang II.

FIG. 2C. $CB_1R$ antagonist prevents CGS21680 mediated pERK in eHSCs. eHSCs were stimulated with CGS21680 (CGS; specific adenosine A2A subtype receptor (A2aR) agonist) in the absence or presence of SR. Lysates were subjected to SDS-PAGE and immunoblotting. The levels of Ang II- or CGS-mediated pERK normalized to total ERK are indicated. Western blot data are expressed as the mean±SD (n=3-4). * $p<0.05$; ** $p<0.01$, Student's t test.

FIG. 3A. $CB_1R$ activation regulates Ang II-mediated increase in pERK in HEK293 cells. HEK293 transfected with AT1R alone or together with $CB_1R$ plasmids were stimulated with 10 nM Ang II for 3 minutes, in the absence or presence of SR141716 (SR; 1 μM); or THL (1 μM; 1 hour pre-treatment). ERK phosphorylation was assessed by Western blot using antibodies to pERK and ERK. Data represent mean±SEM (n=4).

FIG. 3B. Functional interaction between $CB_1R$ and AT1R. The levels of Ang II-mediated pERK normalized to total ERK are summarized under various treatments, after 10 nM Ang II stimulation for 3 minutes.

FIGS. 3C and 3D. Endocannabinoid-mediated $CB_1R$ basal activity allows Ang II-mediated pERK. PhosphoERK levels after Ang II stimulation were examined in Neuro2A-AT1R cells, after treatment with the diacylglycerol lipase inhibitor THL alone or together with Hu210 (0.1 nM) (FIG. 3C); or with increasing concentrations of 2-AG (FIG. 3D). Lysates were subjected to SDS-PAGE and immunoblotting. Data are expressed as the mean±SD (n=3-4).

FIG. 3E. Association with $CB_1R$ affects AT1R G protein coupling. PhosphoERK (pERK) levels after Ang II stimulation were examined in Neuro2A-AT1R cells, after incubation with pertussis toxin (PTX) without or with RNAi-mediated $CB_1R$ downregulation; after transfection with a Gαq dominant negative construct (DN Gαq) without or with RNAi-mediated $CB_1R$ downregulation.

FIG. 4A. $CB_1R$ antagonist prevents Ang II-mediated fibrogenic response in eHSC. eHSCs were stimulated with Ang II in the absence or presence of SR141716 (SR) for 4 hours before the RNA was harvested.

FIG. 4B. $CB_1R$ antagonist prevents CGS21680 (CGS)-mediated fibrogenic response in eHSC. eHSCs were stimulated with CGS in the absence or presence of SR for 6 hours before the RNA was harvested.

FIG. 4C. $CB_1R$ antagonist prevents CGS-mediated fibrogenic response in mouse fibrotic liver. $CCl_4$- or vehicle-treated mice were injected intraperitoneally (i.p.) with vehicle, CGS, or CGS+AM 251 (AM, $CB_1R$ antagonist). After 6 hours, the mice were sacrificed, their liver quickly removed and the RNA harvested.

FIG. 8A-8G. Characterization of CB1R-AT1R Antibody Binding Specificity and Biological Activity.

FIG. 8A. Detection of AT1R-CB1R heteromers with heteromer-selective monoclonal antibodies. Receptor abundance was determined in Neuro2A, Neuro2A-AT1R and Neuro2A-AT1R cells where CB1R was downregulated by RNAi (Neuro2A-AT1R siCB1R) with a monoclonal antibody to AT1R-CB1R, or polyclonal antibodies to AT1R or to CB1R by ELISA. Results are means±SEM (n=3 experiments). ***, p<0.001; n.s., non-significant, vs Neuro2A-AT1R.

FIG. 8B. HEK293 cells were transfected with plasmids coding for CB1R and AT1R, alone or in combination. Receptor abundance was determined with the monoclonal antibody to AT1R-CB1R, or polyclonal antibodies to AT1R or to CB1R by ELISA. Results are means±SEM (n=3).

FIG. 8C. HEK293 cells transfected with plasmids coding for the indicated GPCRs were incubated with the antibody to AT1R-CB1R and subjected to ELISA. Results are means±SEM (n=3).

FIG. 8D. HEK293 cells were transfected with different ratios of the plasmids coding for Myc-CB1R and Flag-AT1R, as indicated. The cells were incubated with the indicated antibodies and subjected to ELISA. Results are means±SEM (n=3).

FIG. 8E. Detection of AT1R-CB1R heteromers with heteromer-selective monoclonal antibodies in the activated hepatic stellate cells (eHSCs). Receptor abundance was determined in cHSCs and eHSCs with a monoclonal antibody to AT1R-CB1R by ELISA. Results represent the means±SEM obtained with antibodies from 7 different hybridoma clones. ***, p<0.001.

FIG. 8F. CB1R-AT1R mediated activity can be selectively blocked by heteromer specific antibody. Neuro-2A cells (40,000 cells/well) endogenously expressing CB1R and transfected with AT1R were preincubated without or with heteromer antibodies followed by treatment with 1 μM Ang II (AT1R agonist) in the absence or presence of 10 nM AM (CB1R antagonist) and pERK levels were determined by Western blotting.

FIG. 8G. Inhibition of AT1R-CB1R signaling by the AT1R-CB1R heteromer antibody. Neuro2A-AT1R and Neuro2A-AT1R cells where CB1R was downregulated by RNAi (Neuro2A-AT1R/siCB1R) were incubated with increasing concentrations of the monoclonal anti-AT1R-CB1R antibody (hydridoma supernatant, +, 1:20 v/v; ++, 1:10 v/v; +++, 1:5 v/v; ++++, 2:5 v/v) for 30 minutes, and then were stimulated with 10 nM Ang II for 3 minutes. Cell lysates and media were subjected to Western blotting analysis using antibodies to pERK and ERK (1:1,000) (lysate) and anti-mouse IgG (media). Imaging and quantification was carried out using the Odyssey Imaging system (Li-Core Biosciences). Results are means±SEM (n=4 experiments). ***, p<0.001; n.s., non-significant, vs the corresponding Ang II treatment.

FIGS. 9A-9D: Characterization of Ang II-mediated increased in pERK in Neuro2A-AT1R cells. Data represent mean±SEM (n=2-5).

FIG. 9A. Association of AT1R and $CB_1R$ in Neuro2A-AT1R. Lysates from Neuro2A and Neuro2A-AT1R were subjected to immunoprecipitation using a protein A-agarose coupled-anti-$CB_1R$ antibody, and to Western blotting. AT1R is detected in the $CB_1R$ immunoprecipitate from Neuro2A-AT1R.

FIG. 9B. Time course of Ang II-mediated increase in pERK. Neuro2A-AT1R cells were stimulated with 10 nM Ang II in the absence or presence of the AT1R specific antagonist Losartan (1 μM) for the indicated times.

FIG. 9C. Dose response of ERK phosphorylation to Ang II treatment in Neuro2A-AT1R. Cells were stimulated with increasing concentration of Ang II for 3 minutes. It is to be noted that concentrations of Ang II superior to 10 nM lead to a decrease in pERK levels, demonstrating a desensitization of the pathway leading to ERK phosphorylation at high concentrations.

FIG. 9D. Influence of $CB_1R$ on Ang II-mediated increase in pERK. Neuro2A-AT1R transfected or not with a siRNA to $CB_1R$, or Neuro2A (wild type) cells were stimulated with 10 nM Ang II for the indicated times. ERK phosphorylation was assessed by Western blot using antibodies to pERK and ERK.

FIGS. 10A-10C: $CB_1R$ regulates Ang II-mediated increase in pERK. ERK phosphorylation was assessed by Western blot using antibodies to pERK and ERK. Data represent mean±SEM (n=3-5).

FIG. 10A. Dose response of ERK phosphorylation to Ang II treatment in Neuro2A-AT1R transfected or not with a siRNA to $CB_1R$.

FIG. 10B. Dose response of ERK phosphorylation to Ang II treatment in the presence of $CB_1R$ antagonist (SR141716; 1 μM).

FIG. 10C. Dose response of ERK phosphorylation to Ang II treatment in the presence of a non-signaling dose of the $CB_1R$ agonist (Hu210; 0.1 nM). Cells were stimulated with increasing concentration of Ang II.

FIG. 11A. Dose response of ERK phosphorylation to Ang II treatment in Neuro2A-AT1R transfected or not with a siRNA to $CB_1R$ and treated or not with Pertussis Toxin (PTX, 15 nM, 16 hours).

FIG. 11B. Dose response of ERK phosphorylation to Ang II treatment in Neuro2A-AT1R transfected or not with a dominant negative Gαq construct alone or together with a siRNA to $CB_1R$.

FIG. 11C. Dose response of ERK phosphorylation to Ang II treatment in Neuro2A-AT1R treated with vehicle or forskolin (1 μM, 30 min).

FIG. 11D. Dose response of ERK phosphorylation to Ang II treatment in Neuro2A-AT1R transfected or not with a siRNA to βarrestin2.

FIG. 12A. Ultrastructural analysis depicting micro- and macrovesicular steatosis, vacuolization, and electron dense mitochondria in livers from ethanol fed rats (right panel) compared to livers from control rats (left panel) (magnification=2500×).

FIG. 12B. Light micrographs from HSC isolated from control and ethanol-fed rats.

DETAILED DESCRIPTION OF THE INVENTION

Figure 1A:
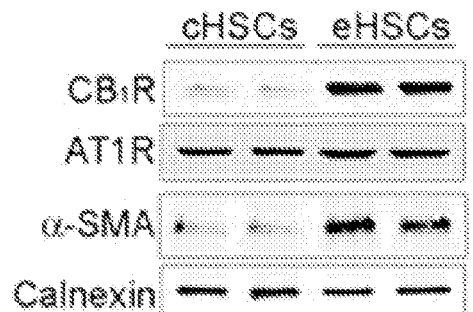

The present invention is related to compounds and compositions thereof, useful for the treatment of liver disease and methods of treating liver disease. The present invention also relates to methods of screening for compounds useful for the treatment of liver disease. The present invention also relates to methods of screening for diacylglycerol lipase inhibitors.

The present invention demonstrates that there is enhanced, fibrosis-specific association of $CB_1R$ with angiotensin II receptor (AT1R) and with adenosine A2A receptors. These complexes have a unique tissue localization and expression during a pathological state (namely, liver fibrosis). Therefore, drugs targeting these receptor complexes will have enhanced selectivity (both spatial and temporal) with potentially fewer side effects and undesired properties than drugs targeting either of the heteromer components individually, out of the context of the heteromer (e.g., as monomers or homodimers). This finding has resulted in the identification of novel compounds and methods of treating liver diseases, such as cirrhosis and fibrosis, and novel methods of identifying compounds useful for the treatment of liver disease.

The endocannabinoid 2-AG is highly upregulated during chronic liver diseases and is implicated in the pathogenesis of non-alcoholic fatty liver disease, progression of fibrosis to cirrhosis and the development of the cardiovascular abnormalities of cirrhosis, such as the hyperdynamic circulatory syndrome and cirrhotic cardiomiopathy. The design or identification of compounds that inhibits 2-AG activity is important for the treatment of such conditions. The present invention also provides for a receptor complex system in which ERK1/2 phosphorylation can be controlled in a concentration-dependent manner by 2-AG.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

A "heteromer" is a protein complex formed from two or more different types of subunits or components. A GPCR heteromer is a complex formed from two or more different GPCR molecules (protomers). In a specific embodiment, a heteromer is a heterodimer. In preferred embodiments, a heteromer comprises: $CB_1R$ complexed with angiotensin II receptor (AT1R)($CB_1$R-AT1R) or with adenosine A2A receptors ($CB_1$R-A2aR).

The term "inhibiting" a heteromer is meant to include inhibiting at least one function or formation of the heteromer. For example, inhibiting the activity of a $CB_1$R-AT1R heteromer, includes, among others, inhibiting formation of the complex, inhibiting ERK phosphorylation, and the like. Assays to measure the different activities of heteromers and their inhibition are described in detail in the examples section which follows.

"Endocannabinoid activity" refers to any one or more in vivo functions of the molecules involved in endocannabinoid system, for example, stimulation of $CB_1R$ resulting in activation of the ERK1/2 pathway. The endocannabinoid system refers to a group of neuromodulatory lipids and their receptors that are involved in a variety of physiological processes including appetite, pain-sensation, mood, and memory. It is named for endocannabinoids, the endogenous lipids that bind cannabinoid receptors (the same receptors that mediate the psychoactive effects of cannabis). Broadly speaking, the endocannabinoid system refers to: the cannabinoid receptors CB1 and CB2, two G protein-coupled receptors primarily located in the central nervous system and periphery, respectively. The endogenous arachidonate-based lipids, anandamide(N-arachidonoylethanolamine (AEA)) and 2-arachidonoylglycerol (2-AG), collectively termed the "endocannabinoids", that are ligands for the cannabinoid receptors. Enzymes synthesize and degrade the endocannabinoids anandamide and 2-AG. Unlike neurotransmitters, endogenous cannabinoids are not stored in vesicles after synthesis, but are synthesized on demand. In preferred embodiments, the compounds of the invention, modulate or inhibit endocannabinoid activity for the treatment of liver fibrosis, liver diseases, obesity, metabolic syndrome, pain, affective and neurodegenerative disorders, inflammation.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term "antibody", is inclusive of all species, including human and humanized antibodies. The antigenic target, for example, $CB_1$R-AT1R heteromers, $CB_1$R-A2aR heteromers, can be also be from any species. Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_{H-CH1}$ by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term "antibody", as used herein also includes antibody fragments either produced by the modification of whole antibodies or synthesized de novo using recombinant DNA methodologies. Embodiments include single chain antibodies, single chain Fv (scFv) antibodies in which a variable heavy and a variable light chain are joined together (directly or through a peptide linker) to form a continuous polypeptide.

An "antigen-binding site" or "binding portion" refers to the part of an immunoglobulin molecule that participates in antigen binding. The phrase "specifically binds to" when referring to an antibody refers to a binding reaction which is determinative of the presence of the protein or peptide in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies specific for $CB_1$R-AT1R heteromers or $CB_1$R-A2aR heteromers can be raised to the $CB_1$R-AT1R heteromers or $CB_1$R-A2aR heteromers peptides that specifically bind to each heteromer protein or peptides thereof, and not to other proteins present in a tissue sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity. As used herein, the term "binding affinity" refers to the non-covalent interactions of the type which occur between an immunoglobulin molecule and an antigen for which the immunoglobulin is specific. The strength or binding affinity of immunological binding interactions can be expressed in terms of the dissociation constant (Kd) of the interaction, wherein a smaller Kd represents a greater affinity. Binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity and is thus equal to the dissociation constant Kd. See, generally, Davies et al. *Ann. Rev. Biochem.*, 59: 439-473 (1990). In one embodiment, the invention includes antibodies that bind to the heteromers with very high affinities (Kd). For example a human, rabbit, mouse, chimeric or humanized antibody that is capable of binding CB1R-AT1R heteromers or CB1R-A2aR heteromers with a Kd less than, but not limited to, $10^{-5}$, $10^{-6}$, $10^{-7}$, $10^{-8}$, $10^{-9}$, $10^{-10}$ or $10^{-11}$ M, or any range or value therein. Thus, an antibody with a "high-affinity" is an antibody having a Kd, or dissociation constant, in the nanomolar (nM) range or better. A Kd in the "nanomolar range or better" may be denoted by X nM, where X is a number less than about 10. Affinity and/or avidity measurements can be measured by ligand binding assays, KinExA™ and/or BIACORE™.

The antibody specificities are also meant to encompass any variants, mutants, derivatives, alleles, isoforms, orthologs, fragments of $CB_1$R-AT1R heteromers or $CB_1$R-A2aR heteromers. Thus, an antibody or antigen-binding portion thereof of the invention specifically binds to the heteromer of $CB_1R$/AT1R or $CB_1R$/A2aR, rather than to monomers or homodimers of the components of the complex (i.e., the antibody or antigen-binding portion thereof specifically recognizes an epitope that is only available when the heteromer complex is formed). The increase in binding of the antibody to the heteromer complex compared to binding to monomers or homodimers of CB1R or AT1R is at least about 5-fold. The antibodies preferably bind to the heteromers rather than the monomers.

The terms "monoclonal antibody" and "monoclonal antibody composition" as used herein, refer to a preparation consisting of a single species of antibody molecules with a single binding specificity and affinity for a particular epitope within the antigen. A monoclonal antibody refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof, mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). Additionally, techniques for the production and isolation of monoclonal antibodies and antibody fragments are known in the art, and are generally described, among other places, in Harlow and Lane, Antibodies: A Laboratory Manual, Cold Spring Harbor Laboratory, 1988, and in Goding, Monoclonal Antibodies: Principles and Practice, Academic Press, London, 1986.

The term "human monoclonal antibody" or "humanized antibodies" refers to monoclonal antibodies that have variable and constant regions (if present) derived from human germline immunoglobulin sequences. "Humanized" antibodies refer to molecules having an antigen binding site that is substantially derived from an immunoglobulin from a non-human species and the remaining immunoglobulin structure of the molecule based upon the structure and/or sequence of a human immunoglobulin. The antigen binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody. Human monoclonal antibodies can be produced by standard methodologies, including though the preparation of an appropriate hybridoma.

The term "epitope" includes any molecular (e.g., protein) determinant capable of being specifically bound by an immunoglobulin molecule or T-cell receptor. Epitopic determinants usually consist of chemically active surface groupings of molecules, such as amino acids or sugar side chains, and usually have specific three dimensional structural characteristics, as well as specific charge characteristics.

The term "agonist" or "agonist-like" as used herein means that upon the binding of an anti-$CB_1R$/GPCR heteromer antibody of the present invention (e.g., anti-$CB_1R$/AT1R or $CB_1R$/A2aR heteromer antibody) or antigen-binding portion thereof, to the $CB_1R$/AT1R or $CB_1R$/A2aR heteromer ("the antibody target"), at least one biological effect typically observed when a natural ligand of the target heteromer binds to the receptor complex in vivo is induced. For example, an anti-$CB_1R$/AT1R heteroimer antibody having an agonist-like effect will induce at least one biological effect typically observed following stimulation of the heteromer by 2-AG, a natural ligand of the receptor complex. Such an effect can be, for example, a decrease in the production of intracellular cAMP.

The term "antagonist" or "antagonist-like" as used herein means that upon the binding of an anti-$CB_1R$/GPCR heteromer antibody of the present invention (e.g., anti-$CB_1R$/AT1R or $CB_1R$/A2aR heteromer antibody) or antigen-binding portion thereof, to the antibody target, at least one biological effect typically observed when a natural ligand of the target heteromer binds to the receptor complex in vivo is inhibited partially or fully. For example, an anti-$CB_1R$/AT1R heteromer antibody having an antagonist-like effect will reduce or inhibit at least one biological effect typically observed following stimulation of the heteromer by 2-AG, a natural ligand of the receptor complex. Such an effect can be, for example, a decrease the production of intracellular cAMP normally induced by an agonist of the subject heteromer complex.

As used herein, the terms "isolated" and "isolating" mean that the referenced material is removed from its native environment, e.g., a cell. Thus, an isolated biological material can be free of some or all cellular components, i.e., components of the cells in which the native material naturally occurs (e.g., a cytoplasmic or membrane component).

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

The term "liver disease" includes diseases and conditions of the liver including liver cirrhosis, alcoholic and non-alcoholic fibrosis as well as to liver disease or changes associated with obesity, diabetes and metabolic syndrome. Other examples of liver diseases include: hepatitis, fatty liver, toxic liver failure, hepatic cirrhosis, diabetes-associated liver disease, liver steatosis, liver fibrosis, liver cirrhosis, chronic hepatitis and the like.

As used herein, the term "test substance" or "candidate therapeutic agent" or "agent" or "compound" are used interchangeably herein, and the terms are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. A test substance or agent can be assayed in accordance with the methods of the invention at any stage during clinical trials, during pre-trial testing, or following FDA-approval.

As used herein, "modulation" means either an increase (stimulation) or a decrease (inhibition) in the expression, in vivo amounts of a target molecule, e.g. $CB_1R$-AT1R heteromers, $CB_1R$-A2aR heteromers. This includes any amounts in vivo, functions and the like as compared to normal controls. The term includes, for example, increased, enhanced, increased, agonized, promoted, decreased, reduced, suppressed blocked, or antagonized. Modulation can increase activity or amounts more than 1-fold, 2-fold, 3-fold, 5-fold, 10-fold, 100-fold, etc., over baseline values. Modulation can also decrease its activity or amounts below baseline values.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

The term "sample" is meant to be interpreted in its broadest sense. A "sample" refers to a biological sample, such as, for example; one or more cells, tissues, or fluids (including, without limitation, plasma, serum, whole blood, cerebrospinal fluid, lymph, tears, urine, saliva, milk, pus, and tissue exudates and secretions) isolated from an individual or from cell culture constituents, as well as samples obtained from, for example, a laboratory procedure. A biological sample may comprise chromosomes isolated from cells (e.g., a spread of metaphase chromosomes), organelles or membranes isolated from cells, whole cells or tissues, nucleic acid such as genomic DNA in solution or bound to a solid support such as for Southern analysis, RNA in solution or bound to a solid support such as for Northern analysis, cDNA in solution or bound to a solid support, oligonucleotides in solution or bound to a solid support, polypeptides or peptides in solution or bound to a solid support, a tissue, a tissue print and the like. Numerous well known tissue or fluid collection methods can be utilized to collect the biological sample from the subject in order to determine the level of DNA, RNA and/or polypeptide of the variant of interest in the subject. Examples include, but are not limited to, fine needle biopsy, needle biopsy, core needle biopsy and surgical biopsy (e.g., brain biopsy), and lavage. Regardless of the procedure employed, once a biopsy/sample is obtained the level of the variant can be determined and a diagnosis can thus be made.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

The phrase "therapeutically effective amount" means an amount of a compound or a combination of compounds that ameliorates, attenuates or eliminates one or more of the symptoms of a particular disease or condition or prevents, modifies, or delays the onset of one or more of the symptoms of a particular disease or condition. Thus, a therapeutically effective amount/dose refers to the amount/dose of a pharmaceutical composition of the invention that is suitable for treating a patient or subject having, for example, a liver disease such as liver fibrosis or cirrhosis. In certain embodiments of the invention the patient or subject may be a mammal. In certain embodiments, the mammal may be a human.

As used herein, the term "animal" or "patient" is meant to include, for example, humans; domestic, veterinary or farm animals such as, for example, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

The term "$ED_{50}$" means the dose of a drug that produces 50% of its maximum response or effect.

The term "$IC_{50}$" means the concentration of a drug which inhibits an activity or property by 50%, e.g., by reducing the frequency of a condition, such as cell death, by 50%, by reducing binding of a competitor peptide to a protein by 50% or by reducing the level of an activity by 50%.

The term "$LD_{50}$" means the dose of a drug that is lethal in 50% of test subjects.

"Composition" indicates a combination of multiple substances into an aggregate mixture.

Screening Assays

In the present invention, methods of screening for a compound that is useful for the treatment of liver disease are provided. In certain embodiments, such methods are useful for identifying a compound that specifically binds to the $CB_1R$/adenosine 2a receptor (A2aR) heteromer. These methods include the steps of: a) mixing the compound with the $CB_1R$/A2aR heteromer, $CB_1R$ monomers, $CB_1R$ homodimers, A2aR monomers, and A2aR homodimers, b) measuring the amount of compound bound to the $CB_1R$/A2aR heteroer, $CB_1R$ monomers, $CB_1R$ homodimers, A2aR monomers, and A2aR homodimers, and c) selecting as a compound that specifically binds to the $CB_1R$/A2aR heteromer as compared to binding to control receptors such as, for example, $CB_1R$ monomers, $CB_1R$ homodimers, A2aR monomers, or A2aR homodimers. Preferably, the compound inhibits the activity of the heteromers. The activity can include heteromers complex formation, phosphorylation of ERK etc.

In certain aspects of the present invention, the methods for screening a compound that is useful for the treatment of liver disease may also be carried out using the $CB_1R$/angiotensin II receptor (AT1R) heteromer. Similarly, such methods are useful for identifying a compound that specifically binds to the $CB_1R$/AT1R heteromer as compared to each monomer subunit. These methods include the steps of: a) mixing the compound with the $CB_1R$/AT1R heteromer, $CB_1R$ monomers, $CB_1R$ homodimers, AT1R monomers, and AT1R homodimers, b) measuring the amount or of compound bound to the $CB_1R$/AT1R heteromer, $CB_1R$ monomers, $CB_1R$ homodimers, AT1R monomers, and AT1R homodimers, and c) selecting as a compound that specifically binds to the $CB_1R$/AT1R heteromer and inhibits the activity of the heteromers as compared to binding to control receptors such as, for example, $CB_1R$ monomers, $CB_1R$ homodimers, AT1R monomers, or AT1R homodimers.

In certain embodiments of the present invention, specific binding of a screening compound of the invention to the $CB_1R$/AT1R and/or $CB_1R$/A2aR heteromers is measured by a classical ligand binding assay. For example, a ligand binding assay may be carried out in cells, such as, for example, CHO, HEK293, COS cells, and the like, expressing only $CB_1R$, only AT1R, only A2aR, or co-expressing $CB_1R$/AT1R or $CB_1R$/A2aR. A detailed protocol for a ligand binding assay is provided in the Examples section which follows.

Specific binding of a compound to heteromers of the invention ($CB_1R$/A2aR or $CB_1R$/AT1R) i.e., a composition exhibiting a higher affinity as compared to a control, is preferably at least about 5 fold greater, more preferably at least about 10 fold greater, and most preferably at least about 20 fold greater than binding to the homodimers or monomers of the members comprising the heteromer to which the composition binds (e.g., of A2aR, AT1R or $CB_1R$). In another preferred embodiment, a compound may inhibit the function or activity of any of the heteromers by modulating one or more activities, such as for example, signaling, phosphorylation of ERK, endocannabinoid activity, profibrogenic activity, binding of ligands to the heteromer, and the like.

The term "compound" is meant to cover any molecule or molecules that modulate the function or activities in vivo or in vitro, of the $CB_1R$/AT1R and/or $CB_1R$/A2aR heteromers, including the inhibition of heteromer formation. The compounds are specific for the heteromers as compared to the monomer subunits or control receptors, e.g. $CB_1R$ monomers, $CB_1R$ homodimers, AT1R monomers, AT1R homodimers, A2aR monomers, or A2aR homodimers. Examples of compounds comprise: aptamers, antibodies, small molecules, nucleic acids, proteins, peptides, polypeptides, peptidomimetics, peptoids enzymes, organic or inorganic molecules, synthetic molecules, natural molecules, or combinations thereof.

In other aspects of the invention, compounds are screened for the ability to specifically inhibit $CB_1R$/AT1R and/or $CB_1R$/A2aR heteromers over homodimers or monomers of the members comprising the heteromer to which the composition binds (e.g., of A2aR, AT1R or $CB_1R$). Preferably, antagonist or inhibitory activity of a compound that specifically inhibits a heteromer of the invention (e.g., the $CB_1R$/AT1R and/or $CB_1R$/A2aR heteromer) is about at least about 2-fold greater, more preferably at least about 5-fold greater, and most preferably at least about 10-fold greater than the antagonist or inhibitory activity of the same composition against homodimers or monomers of the members comprising the heteromer to which the composition binds (e.g., of A2aR, AT1R or $CB_1R$).

In certain embodiments of the invention, methods of screening for a compound useful for the treatment of liver disease are provided, wherein such methods include selecting compounds that inhibit endocannabinoid activity in cells engineered to express $CB_1R$/AT1R heteromer, wherein such inhibition is greater than the inhibition of endocannabinoid activity in cells engineered to express $CB_1R$ alone or AT1R alone. In certain aspects, this screening assay is carried out in HEK293 or CHO cells. In yet other aspects, the cells for use in the screening assay may alternatively express the $CB_1R$/A2aR heteromer. Also Neuro2A cells stably expressing AT1R or A2aR can be used in the screening assay since they express endogenous CB1R, and therefore will express CB1R/AT1R or CB1R/A2aR heteromers.

In one aspect of the invention, inhibition of endocannabinoid activity is determined by measuring ERK1/2 phosphorylation. Importantly, in the $CB_1R$/AT1R heteromeric complex, angiotensin II (Ang II), an agonist of AT1R, can stimulate ERK1/2 phosphorylation when $CB_1R$ is stimulated (with endocannabinoids/cannabinoid agonists, e.g., 2-AG). Thus, inhibition of endocannabinoid activity is accompanied by a decrease in ERK1/2 phosphorylation. ERK1/2 phosphorylation may be determined by Western blot of whole cell lysates using a phospho-ERK (pERK) specific antibody. These methods are well known by those skilled in the art.

Preferably, the inhibition of endocannabinoid-mediated ERK phosphorylation in cells expressing the $CB_1R$/AT1R is about at least about 20 fold greater than the inhibition of endocannabinoid-mediated ERK phosphorylation in cells engineered to express $CB_1R$ alone or AT1R alone.

In certain embodiments of the present invention, methods of screening for a compound useful for the treatment of liver disease are provided. In some aspects, these methods include selecting compounds that decrease intracellular cAMP levels in cells engineered to express a $CB_1R$/AT1R heteromer. When AT1R heterodimerizes with $CB_1R$, it couples to inhibitory G protein (Gi). Gi reduces the levels of intracellular cAMP. Thus, activation of AT1R within the $CB_1R$-AT1R complex leads to reduction in intracellular cAMP levels. Selective ligands for $CB_1R$-AT1R may be identified by measuring the ability of the ligand or small molecule to decrease intracellular cAMP. In some embodiments of the invention, the decrease in intracellular cAMP levels is greater than the decrease in intracellular cAMP levels in cells engineered to express $CB_1R$ alone or AT1R alone. The levels of intracellular cAMP may be determined using commercially available detection kits, such as the one sold by Millipore (Billerica, Mass. 01821), Invitrogen (Carlsbad Calif. 92008), Perkin Elmer (Waltham, Mass. 02451) etc.

A compound selected as a useful for treating liver disease in this assay will preferably cause a decrease in intracellular cAMP levels in cells expressing the $CB_1R$/AT1R heteromer of at least about 5 fold greater than the decrease in intracellular cAMP levels in cells engineered to express $CB_1R$ alone or AT1R alone.

In certain aspects of the present invention, methods of screening for a diacylglycerol lipase (DAGL) inhibitor are provided. In certain aspects, these methods include selecting compounds that decrease ERK1/2 phosphorylation in cells expressing $CB_1R$ and another G-protein coupled receptor (GPCR). In certain aspects, these receptors are only capable of inducing ERK1/2 phosphorylation when the ligand for both the $CB_1R$ and the non-related GPCR are present together. Examples of the other GPCR in a complex with $CB_1R$ are AT1R and A2aR. In certain embodiments, the receptor ligands, e.g., 2-AG and angiotensin II (for the $CB_1R$/AT1R heteromer) or 2-AG and adenosine (for the CB1R/A2aR heteromer) are mixed with the screening composition and added to the test cells.

In some embodiments, the cells that may be used for this assay include but are not limited to: Neuro2A, HEK293 cells, CHO cells and the like.

ERK1/2 phosphorylation may be determined by Western blot or any other method known in the art for determining the level of phosphorylated protein in a sample, such as a cell lysate. Such methods are described in detail in Rozenfeld and Devi, 2007 (Receptor heteromerization leads to a switch in signaling: beta-arrestin2-mediated ERK activation by mu-delta opioid receptor heteromers. Rozenfeld R, Devi L A. *FASEB J.* 2007 August; 21(10):2455-65).

In other aspects, the DAGL screening assay may be conducted as a high-throughput screen of small molecules, such as drug-like pharmacophores.

In another preferred embodiment, methods (also referred to herein as "screening assays") are provided for identifying candidate or test compounds or agents which modulate the expression, function, activity of the heteromers, e.g. $CB_1R$-AT1R heteromers, $CB_1R$-A2aR heteromers. Compounds thus identified can be used to modulate the activity of target gene products, e.g. $CB_1R$-AT1R heteromer, $CB_1R$-A2aR heteromer gene products, in a therapeutic protocol, to modulate the biological function of the target gene product, or to identify compounds that disrupt normal target interactions.

After identifying a test compound or candidate agent as an agonist and/or an antagonist, the compound may then be used to treat subjects with diseases and disorders associated with $CB_1R$-AT1R heteromers, $CB_1R$-A2aR heteromers.

Candidate agents also include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA. These molecules can be natural, e.g. from plants, fungus, bacteria etc., or can be synthesized or synthetic.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the one-bead one-compound library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci.* USA 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Nat'l Acad Sci* USA 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

A prototype compound may be believed to have therapeutic activity on the basis of any information available to the artisan. For example, a prototype compound may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against hepatitis virus, liver cancer, liver inflammation, cirrhosis or any combination thereof. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate compounds can be isolated, from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomer, or small molecule libraries of compounds and are preferred approaches in the present invention. See Lam, *Anticancer Drug Des.* 12: 145-167 (1997).

In an embodiment, the present invention provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate the protein or peptide intracellular persistence may comprise, for example, evaluation of intracellular residence time or half-life in response to a candidate therapeutic agent. In a preferred embodiment, the half-life of a protein or peptide in the presence or absence of the candidate therapeutic compound in human tissue is determined. Half-life may be determined in any tissue. Any technique known to the art worker for determining intracellular persistence may be used in the present invention. By way of non-limiting example, persistence of a compound may be measured by retention of a radiolabeled or dye labeled substance.

A further aspect of the present invention relates to methods of inhibiting the activity of a condition or disease comprising the step of treating a sample or subject believed to have a disease or condition with a prodrug identified by a compound of the invention. Compositions of the invention act as identifiers for prodrugs that have therapeutic activity against a disease or condition. In a preferred aspect, compositions of the invention act as identifiers for drugs that show therapeutic activity against conditions including for example cancer.

In one embodiment, a screening assay is a cell-based assay in which a cell expresses a $CB_1R$-AT1R heteromer or peptides thereof, or $CB_1R$-A2aR heteromers or peptides, $CB_1R$-AT1R-detectable marker construct or fusion protein construct, for example, GST, luciferase fusion partners, isoforms or mutants thereof, which is contacted with a test compound, and the ability of the test compound to modulate the expression and/or activity of the respective heteromers. Determining the ability of the test compound to modulate can be accomplished by monitoring, for example, immunoassays, blots, pull-down assays, etc, assays described in detail in the Examples section which follows. The cell, for example, can be of mammalian origin, e.g., human.

In another preferred embodiment, the screening assay is a high-throughput screening assay.

In another preferred embodiment, soluble and/or membrane-bound forms of isolated proteins, mutants or biologically active portions thereof, can be used in the assays if desired. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays can also be used and involve preparing a reaction mixture of the target gene or gene products thereof, and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al, U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

In another embodiment, determining the ability of a protein to bind or "dock" to a target molecule or docking site on a target molecule can be accomplished using real-time Biomolecular Interaction Analysis (BIA) (see, e.g., Sjolander, S, and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target product or the test substance is anchored onto a solid phase. The target product/test compound complexes anchored on the solid phase can be detected at the end of the reaction. Preferably, the target product can be anchored onto a solid surface, and the test compound, (which is not anchored), can be labeled, either directly or indirectly, with detectable labels discussed herein.

Libraries: Candidate agents may be also be obtained from a wide variety of libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries: Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinational chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci* USA. 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol. Divers.* 2:223-36, 1997; Fauchere et al., Peptide and nonpeptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci.* USA, 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.*, 114:9217-9218 (1992)); analogous organic syntheses of small compound libraries (Chen, et al., *J. Amer. Chem. Soc.*, 116:2661 (1994)); oligocarbamates (Cho, et al., *Science*, 261: 1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology*, 14(3):309-314 (1996) and PCT/US96/10287); carbohydrate libraries (see, e.g., Liang, et al., *Science*, 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569,588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Small Molecules: Small molecule test compounds can initially be members of an organic or inorganic chemical library. The agonists and antagonists of the present invention can be small molecules. The term "small molecule" as used herein refers to compounds, chemicals, small molecules, small molecule inhibitors, or other factors that are useful for antagonizing or agonizing the target signaling complexes set forth in the invention (e.g. $CB_1R/AT1R$ heteromers, $CB_1R/A2aR$ heteromers, $CB_1R$ only when dimerized with AT1R or A2aR, AT1R only when dimerized with $CB_1R$, or A2aR only when dimerized with $CB_1R$).

These "small molecules" can be small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.*, 1:60 (1997). In addition, a number of small molecule libraries are commercially available.

Diverse libraries of small molecule inhibitors can be generated. The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of potential receptor-heteromer antagonists, can be screened rapidly in high-throughput assays to identify potential lead compounds, as well as to refine the specificity, toxicity, and/or cytotoxic-kinetic profile of a lead compound.

A variety of techniques are available in the art for generating combinatorial libraries of small organic molecules such as the subject antagonists. See, for example, Blondelle et al. (1995) *Trends Anal. Chem.* 14: 83; the Affymax U.S. Pat. Nos. 5,359,115 and 5,362,899: the Ellman U.S. Pat. No. 5,288,514: the Still et al. PCT publication WO 94/08051; Chen et al. (1994) *JACS* 116: 2661: Kerr et al. (1993) *JACS*

115: 252; PCT publications WO92/10092, WO93/09668 and WO91/07087; and the Lerner et al. PCT publication WO93/20242). Accordingly, a variety of libraries on the order of about 100 to 1,000,000 or more diversomers of the subject antagonists can be synthesized and screened for a particular activity or property. These methods are described in detail in U.S. Pat. No. 6,916,821.

Data and Analysis: The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing information over networks such as the Internet.

Compositions

In certain aspects, the present invention provides compositions comprising monoclonal antibodies or small compounds. For example, compositions comprising a $CB_1R/AT_1R$ specific monoclonal antibody are provided. Administration may be achieved by any suitable method.

The compounds of the invention can be formulated for administration in any convenient way for use in human or veterinary medicine. The monoclonal antibodies of the invention may be incorporated into liposomes, microemulsions, micelles, unilamellar or multilamellar vesicles, erythrocyte ghosts or spheroblasts. In one embodiment, the monoclonal antibody and/or small compounds of the invention can be delivered in a vesicle, including as a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, monoclonal antibodies or small compounds of the invention can be delivered in a controlled release form. For example, one or more small compounds may be administered in a polymer matrix such as poly(lactide-co-glycolide) (PLGA), in a microsphere or liposome implanted subcutaneously, or by another mode of delivery (see, Cao et al., 1999, Biomaterials, February; 20(4):329-39). Another aspect of delivery includes the suspension in an alginate hydrogel.

The present invention also provides pharmaceutical formulations or dosage forms for administration to mammals in need thereof.

When formulated in a pharmaceutical composition, the compounds of the present invention can be admixed with a pharmaceutically acceptable carrier or excipient. The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicles with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage from carrier, including but not limited to one or more of a binder (for compressed pills), an encapsulating agent, a flavorant, and a colorant. Suitable pharmaceutical carriers are described in "Remington's Pharmaceutical Sciences" by E. W. Martin.

Administration

The compounds and formulations of the present invention can be administered topically, parenterally, orally, by inhalation, as a suppository, or by other methods known in the art. The term "parenteral" includes injection (for example, intravenous, epidural, intrathecal, intramuscular, intraluminal, intratracheal or subcutaneous). The compounds of the present invention may also be administered using a transdermal patch. In a specific embodiment, the compounds of the present invention are administered via an oral dosage form.

By "transdermal patch" is meant a system capable of delivery of a drug to a patient via the skin, or any suitable external surface, including mucosal membranes, such as those found inside the mouth. Such delivery systems generally comprise a flexible backing, an adhesive and a drug retaining matrix, the backing protecting the adhesive and matrix and the adhesive holding the whole on the skin of the patient. On contact with the skin, the drug-retaining matrix delivers drug to the skin, permitting the drug to pass through the skin into the patient's system.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Administration of the compounds of the invention may be once a day, twice a day, or more often, but frequency may be decreased during a maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

The antagonists described herein can be used to treat or prevent liver diseases, obesity and other metabolic disorders.

The benefit to an individual to be treated is either statistically significant or at least perceptible to the patient or to the physician.

It will be appreciated that the amount of the antagonists of the invention required for use in treatment will vary with the route of administration, the nature of the condition for which treatment is required, and the age, body weight and condition of the patient, and will be ultimately at the discretion of the attendant physician or veterinarian. These compositions will typically contain an effective amount of the compounds of the invention, alone or in combination with an effective amount of any other active material, e.g., those described above. Preliminary doses can be determined according to animal tests, and the scaling of dosages for human administration can be performed according to art-accepted practices.

Keeping the above description in mind, typical dosages of monoclonal antibody may range from about 5 to about 400 mg/h. In certain embodiments, a patient may receive, for example, one or more doses.

An "agonist" is a molecule which activates a certain type of receptor. For example, endocannabinoids act as agonists when they excite cannabinoid receptors. An example of an agonist of the present invention is 2 arachidonoylglycerol (2-AG), which is an agonist of $CB_1R$. AT1R: AngII. CB1R: ACEA: Potent, highly selective CB1 agonist; ACPA: Potent, selective CB1 agonist; Arvani: Potent CB1 and TRPV1 agonist. Also anandamide transport inhibitor; (±)-CP 47497: Potent CB1 agonist; DEA: Endogenous CB1 agonist; Leelamine hydrochloride: CB1 agonist; (R)-(+)-Methanandamid: Potent and selective CB1 agonist; Hu210, 2-AG: non-selective CB1 agonists. A2aR: CGS 21680 hydrochloride: A2A agonist; CV 180: Non-selective adenosine A2 receptor agonist; adenosine: Non-selective adenosine A2 receptor agonist.

By contrast, an "antagonist" is a molecule which prevents or reduces the effects exerted by an agonist on a receptor. An example of an antagonist of the present invention is a monoclonal antibody (mAb) which is generated against the $CB_1R$/AT1R heteromer complex using a subtractive immunization strategy. The mAb preferentially recognizes the $CB_1R$/AT1R heteromer over $CB_1R$ alone or AT1R alone and blocks or decreases the activity of the $CB_1R$/AT1R heteromer. The term "therapeutic index" refers to the therapeutic index (TI) of a drug, defined as $LD_{50}/ED_{50}$. Other examples of antagonists of CB1R, AT1R and A2AR include, for example, Rimonabant (SR141716), CP-945,598, Losartan (Merck, Whitehouse Station, N.J.) etc. A2aR antagonists: SCH 442416: Very selective, high affinity A2A antagonist; SCH 58261: Potent, highly selective A2A antagonist; ZM 241385: Potent, highly selective A2A antagonist (TOCRIS, Ellisville, Mo. 63021). CB1R antagonists: AM 251: Potent CB1 antagonist. Also GPR55 agonist; LY 320135: Selective CB1 receptor antagonist/inverse agonist; O-2050 CB1 silent antagonist. AT1R antagonists: EMD 66684: Potent, selective non-peptide AT1 antagonist; ZD 7155 hydrochloride: Selective non-peptide AT1 antagonist.

Preferred antagonists are those that provide a reduction of activation by the ligand of at least 10%, and more preferably at least 20%, at least 30%, at least 40%, at least 50%, at least 60%, at least 70%, at least 80%, at least 90%, at least 95%, or even at least 99% at a concentration of the antagonist, for example, of 1 µg/ml, 10 µg/ml, 100 µg/ml, 500 µg/ml, 1 mg/ml, 10 mg/ml, or 100 mg/ml. The percentage antagonism represents the percentage decrease in activity of endocannabinoids, e.g., 2-AR, in a comparison of assays in the presence and absence of the antagonist. Any combination of the above mentioned degrees of percentage antagonism and concentration of antagonist may be used to define an antagonist of the invention, with greater antagonism at lower concentrations being preferred.

Antibodies

In a preferred embodiment, a compound comprises an antibody or fragments thereof. Preferably, the antibody is a monoclonal antibody and is specific for $CB_1R$-AT1R heteromers or $CB_1R$-A2aR heteromers as compared to control receptors, for example, $CB_1R$ monomers, $CB_1R$ homodimers, AT1R monomers, AT1R homodimers, A2aR monomers, or A2aR homodimers. Suitable antibodies or antibody fragments may be also be polyclonal, or recombinant. Examples of useful fragments include separate heavy chains, light chains, scFv, Fab, F(ab')2, Fabc, and Fv fragments. Typically, the antibodies, fragments, or similar binding agents bind a specific antigen with an affinity of at least $10^7$, $10^8$, $10^9$, or $10^{10}$ M$^{-1}$.

In certain embodiments, a monoclonal antibody that is specific for a CB1-AT1 heteromer is the antibody designated mAb A108. Monoclonal antibody mAb A108 may be used in any of the compositions and methods described herein and is specifically contemplated for use in such compositions and methods.

Various host animals selected, e.g., from pigs, cows, horses, rabbits, goats, sheep, rats, or mice, can be immunized with a partially or substantially purified epitope peptide identified above, or with a peptide homolog, fusion protein, peptide fragment, analog or derivative thereof. For example, the peptides for immunization can be conjugated to an immune potentiator (such as keyhole limpet hemocyanin (KLH), serum albumin, bovine thyroglobulin, or soybean trypsin inhibitor using a bifunctional or derivatizing agent) to enhance antigen-specific responses. An adjuvant can be used to enhance antibody production. Examples of useful adjuvants include without limitation oil emulsions (e.g., Freund's adjuvant), saponins (e.g., saponin derivative QS-21), aluminium or calcium salts (e.g., alum), non-ionic block polymer surfactants, lipopolysaccharides (e.g., lipopolysaccharide-derived MPL), mycobacteria, tetanus toxoid, MF59 microemulsion, lipid-particle immuno-stimulating complexes (ISCOMs), CpG oligonucleotides and many others (see, e.g., Gupta et al., 1993, *Vaccine*, 11:293-306). Polyclonal antibodies can be obtained and isolated from the serum of an immunized animal.

In a preferred embodiment, an antibody specifically binds to $CB_1R$-AT1R heteromers, proteins, peptides, fragments, variants, orthologs, alleles, isoforms, splice variants, derivatives or mutants thereof as compared to a control receptor, for example, $CB_1R$ monomers, $CB_1R$ homodimers, AT1R monomers, AT1R homodimers.

In a preferred embodiment, an antibody specifically binds to $CB_1R$-A2aR heteromers, proteins, peptides, variants, orthologs, alleles, isoforms, splice variants, fragments, derivatives or mutants thereof, as compared to a control receptor. For example, $CB_1R$ monomers, $CB_1R$ homodimers, A2aR monomers, A2aR homodimers.

Anyone of the antibodies will have applications for research use (ex: Western blots, immunohistochemistry, flow cytometry, imaging, ELISA) as well as clinical applications for prognostics and potential monitoring of therapeutic regimens using automated antibody-based platforms and pathological analysis of patient samples.

Anti-$CB_1R$/GPCR heteromer antibodies or antigen-binding portions of the present invention can have agonist-like and/or antagonist-like properties on $CB_1R$/GPCR heteromers of the invention, such as $CB_1R$/AT1R and $CB_1R$/A2aR heteromers. These antibodies are therefore considered to be agonists or antagonists of their target. Preferably, anti-$CB_1R$/GPCR heteromer antibodies of the invention have an antagonist-like effect (i.e., are antagonists of their target heteromer). Such an antibody or antigen-binding portion would, upon binding to its antigen, exhibit at least one antagonist-like effect. In one embodiment, the antibody or antigen-binding portion of the present invention would exhibit therapeutic effectiveness like an antagonist of $CB_1R$ (e.g., Rimonabant (SR141716)) and also have the ability to reduce undesirable effects of agonists of $CB_1R$/GPCR heteromer (e.g., 2-AG for $CB_1R$/AT1R heteromer) resulting from setting off cascades of second messenger responses (i.e., cAMP increase.). Preferably, the antibody or antigen-binding portion of the present invention exhibits greater therapeutic effectiveness than an antagonist of $CB_1R$ (e.g., Rimonabant (SR141716)), which has undesirable side effects. Such greater therapeutic effectiveness, e.g., for the treatment of liver disease, is achieved by virtue of the specificity of the antibodies of the invention for the $CB_1R$/AT1R or $CB_1R$/A2aR heteromer complex rather than either monomer of the complex alone.

Radiolabeling:

In another preferred embodiment, the antibody of the invention can be radiolabeled. Uses include therapeutic and imaging for diagnostic purposes. The label may be a radioactive atom, an enzyme, or a chromophore moiety. Methods for labeling antibodies have been described, for example, by Hunter and Greenwood, *Nature*, 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci.* USA (1983) 80:4045; Renz and Kurz, *Nucl. Acids Res*. (1984) 12:3435; Richardson and Gumport, *Nucl. Acids Res*. (1983) 11:6167; Smith et al. *Nucl. Acids Res*. (1985) 13:2399; and Meinkoth and Wahl, *Anal. Biochem*. (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, *Proc. Natl. Acad. Sci. USA*, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or biotin-streptavidin, and antibody-antigen.

In another preferred embodiment, the antibody molecules of the invention can be used for imaging. In imaging uses, the complexes are labeled so that they can be detected outside the body. Typical labels are radioisotopes, usually ones with short half-lives. The usual imaging radioisotopes such as $^{123}I$, $^{124}I$, $^{125}I$, $^{131}I$, $^{99m}Tc$, $^{186}Re$, $^{188}Re$, $^{64}Cu$, $^{67}Cu$, $^{212}Bi$, $^{213}Bi$, $^{67}Ga$, $^{90}Y$, $^{111}In$, $^{18}F$, $^{3}H$, $^{14}C$, $^{35}S$ or $^{32}P$ can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Aptamers: CB1R-AT1R or CB1R-A2aR specific molecules can be in the form of aptamers. "Aptamers" are DNA or RNA molecules that have been selected from random pools based on their ability to bind other molecules. The aptamer binds specifically to a target molecule wherein the nucleic acid molecule has sequence that comprises a sequence recognized by the target molecule in its natural setting. Alternately, an aptamer can be a nucleic acid molecule that binds to a target molecule wherein the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art (see, e.g., Gold et al., *Annu. Rev. Biochem.* 64:763, 1995; Brody and Gold, *J. Biotechnol.* 74:5, 2000; Sun, *Curr. Opin. Mol. Ther.* 2:100, 2000; Kusser, *J. Biotechnol.* 74:27, 2000; Hermann and Patel, *Science* 287:820, 2000; and Jayasena, *Clinical Chem.* 45:1628, 1999).

As used herein, the term "aptamer" or "selected nucleic acid binding species" shall include non-modified or chemically modified RNA or DNA. The method of selection may be by, but is not limited to, affinity chromatography and the method of amplification by reverse transcription (RT) or polymerase chain reaction (PCR).

The affinity of aptamers for their target proteins is typically in the nanomolar range, but can be as low as the picomolar range. That is $K_D$ is typically 1 pM to 500 nM, more typically from 1 pM to 100 nM. Apatmers having an affinity of $K_D$ in the range of 1 pM to 10 nM are also useful.

Anti-CB$_1$R/GPCR Heteromer Antibodies

Subtractive Immunization: For induction of tolerance to immunogenic epitopes in HEK-293 membranes, female balb/c mice (6-8 weeks old, 25-35 g body weight) were injected intraperitoneally (i.p.) with 5 mg Neuro-2A membranes and 15 min later with cyclophosphamide (100 mg/kg body weight, i.p.). The cyclophosphamide injection was repeated after 24 and 48 h respectively. Mice were bled every 15 days and antibody titers checked by ELISA against Neuro-2A membranes. This protocol was repeated at 2 week intervals until stable background titers were obtained with Neuro-2A membranes. Mice were then given an i.p. injection of membranes from Neuro-2A cells expressing AT1 angiotensin receptors (5 mg) in complete Freund's adjuvant. Booster i.p. injections of Neuro-2A cells expressing AT1 angiotensin receptors were administered every 15 days. Antibody titers were checked by ELISA against Neuro2A membranes from untransfected cells and from cells expressing AT1 receptors. Spleens from animals giving a high titer with Neuro-2A cells expressing AT1 angiotensin receptors were fused with SP-20 myeloma cells to generate monoclonal antibodies as described (Gupta et al., *JBC* 282:5116, 2007). Clones secreting monoclonal antibodies were screened by ELISA against untransfected Neur-2A membranes, and Neuro-2A cells expressing AT1 angiotensin receptors using 1:10 hybridoma supernatant and 1:500 horse radish peroxidase labeled anti-mouse IgG. Hybridoma supernatant from positive clones was concentrated using Centricon 10 and stored at a concentration of 10 μg protein/μl.

The present invention thus provides isolated monoclonal antibodies and antigen-binding portions thereof that specifically bind to CB1R/AT1R or CB1R/A2aR heteromers. In certain embodiments of the invention, the antibody compositions of the invention exhibit antagonist-like activity on their heteromer targets (CB1R/AT1R or CB1R/A2aR heteromer).

In other aspects of the invention, gene expression is determined using polymerase chain reaction (PCR). PCR is a well-known method that allows exponential amplification of short DNA sequences (usually 100 to 600 bases) within a longer double stranded DNA molecule.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The present invention is described further below in working examples which are intended to further describe the invention without limiting the scope therein.

Materials and Methods

Ligand Binding Assay: Stably transfected cells were seeded in 12-well plates for 24 h. Cells were washed briefly in cold wash buffer (25 mM Tris-HCl, pH 7.4) containing 140 mM NaCl, 5 mM $MgCl_2$, and 0.1% bovine serum albumin (BSA). Binding experiments were performed at 48 C and initiated by the addition of 50 000 cpm of w3Hx-Ang II (69 Ci/mmol) (Amersham Pharmacia Biotech) in the presence of varying amounts of unlabeled Ang II (Sigma, St. Louis, Mo., USA) or compound of interest as a competitor in a 0.5-ml volume of binding buffer w25 mM Tris-HCl buffer, pH 7.4, including 5 mM $MgCl_2$, 0.1% BSA and 100 mg/ml bacitracin (Sigma). Then, 24 h after cold incubation, cells were washed twice in 1 ml of wash buffer and lysed using 0.5 ml of lysis buffer (0.1 M NaOH containing 0.5% of SDS). Receptor-bound radioactivity was determined on a β-counter (Packard Instruments, Downer Grove, Ill., USA) and the binding data ($IC_{50}$ values) were analyzed using GraphPad software (GraphPad Software, San Diego, Calif., USA). To obtain Kd, the Cheng and Prusoff (1973) (*Biochem Pharmacol.* 1973 Dec. 1; 22(23):3099-108) equation was used and Bmax was calculated according to DeBlasi et al. (1989) *Trends Pharmacol Sci.* 10(6):227-9. All measurements are carried out in triplicate and results are expressed as mean±SEM. Statistical significance is evaluated using Student's t-test.

Example 1

CB$_1$R and AT1R Form a Complex in Activated HSCs and CB$_1$R Activity Controls Ang II-Mediated pERK Materials and Methods HSCs from ethanol treated rats were generated in the laboratory of Dr. Natalia Nieto: Rats (300 g female Sprague-Dawley, N=10/group) were fed the control or ethanol Lieber-DeCarli diets for 8 months (Lieber and DeCarli, 1989). Animals received humane care according to the criteria outlined in the Guide for Care and Use of Laboratory Animals. Details regarding pathology of the liver of the control and alcohol fed rats are described in (Cubero and Nieto, 2008;

Urtasun et al., 2009). Briefly, Hematoxylin and eosin staining showed microvesicular and macrovesicular steatosis in livers from ethanol-fed rats; and transaminases and nonesterified fatty acids were elevated twofold and sixfold respectively, in the ethanol-fed rats.

Generation of Ethanol-Treated Rats: Chronic Alcohol Feeding Model. Rats (300 g female Sprague-Dawley, N=10/group) were fed the control or ethanol Lieber-DeCarli diets for 8 months (Lieber C S, DeCarli L M. Liquid diet technique of ethanol administration: 1989 update. *Alcohol Alcohol* 1989; 24: 197-211). Animals received human care according to the criteria outlined in the Guide for Care and Use of Laboratory Animals. ALT, AST, ethanol, and non-esterified fatty acids were assayed using kits from Thermo Electron Corporation (Waltham, Mass.), Sigma (St. Louis, Mo.), and Wako Chemicals (Richmond, Va.), respectively. H&E staining and TEM sections were prepared according to standard methodology and evaluated by a liver pathologist.

Isolation of Hepatic Stellate Cells: These were isolated as described before. (Friedman, S. L. Hepatic stellate cells: protean, multifunctional, and enigmatic cells of the liver. *Physiol Rev* 88, 125-72 (2008); Teixeira-Clerc, F. et al. CB1 cannabinoid receptor antagonism: a new strategy for the treatment of liver fibrosis. *Nat Med* 12, 671-6 (2006)).

Western Blots and Immunoprecipitation: Western blot and phospho-ERK Assays were carried out as described in the case of experiments with Neuro2A cells (Rozenfeld and Devi, 2008). For experiments with HSCs, freshly plated cells were stimulated for 10 minutes with AngII in the presence or absence of SR141716 and THL (as indicated). Phospho ERK and ERK were detected with rabbit monoclonal anti-phospho-p44/42 MAPK (anti-pERK, 1:1000) and mouse monoclonal anti-p44/42 MAPK (anti-ERK, 1:1,000) antibodies. Both blotting and imaging with the Odyssey imaging system (LI-COR, Lincoln, Nebr.) were performed following the manufacturer's protocols. The secondary antibodies that were used included IRDye 680-labeled anti-rabbit antibody, IRDye 800-labeled anti-mouse and anti goat antibodies (1:10,000).

Results $CB_1R$ protein levels exhibited marked upregulation (~7-fold) in HSCs from ethanol treated rats (eHSCs) compared to HSCs from control rats (cHSCs) (FIG. 1A), indicating that, consistent with other experimental models of liver injury, chronic ethanol treatment leads to $CB_1R$ upregulation in HSCs. Activation of the eHSCs was also supported by a substantial increase in the levels of α-smooth muscle actin (α-SMA), a marker of HSC activation (FIG. 1A). However, the expression of a profibrogenic receptor, AT1R, which was also expressed in cHSCs, displayed only a slight increase (<2-fold) in activated HSCs (FIG. 1A).

Figure 1B:
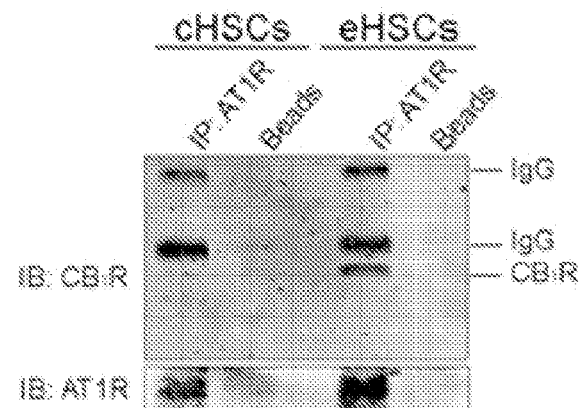

To investigate the influence of upregulated $CB_1R$ on resident AT1R, the direct interaction between the two receptors was examined. It was found that $CB_1R$ can be detected in AT1R-immunoprecipitate in activated but not in control HSCs (FIG. 1B), indicating that the two receptors were present in an interacting complex in activated HSCs.

Figure 1C:
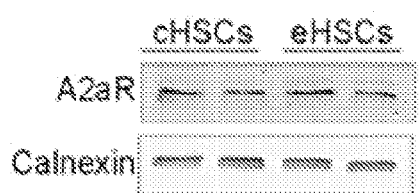
Figure 1D:
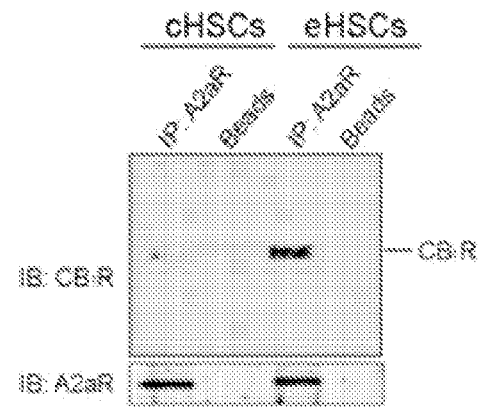

The interaction between CB1R and A2aR was also examined, since stimulation of this receptor activates mitogenic pathways leading to the expression of fibrosis markers (Chan E S, et al., (2006) *Br J Pharmacol* 148:1144-1155; Che J, Chan E S, Cronstein B N (2007). *Mol Pharmacol* 72:1626-1636.) A2aR was constitutively expressed in HSCs, displaying only a slight increase in its levels (~15%) in activated HSCs (FIG. 1C). In these cells, A2aR associated with CB1R since co-immunoprecipitation lead to the isolation of the two receptors in an interacting complex (FIG. 1D).

Figure 1E:
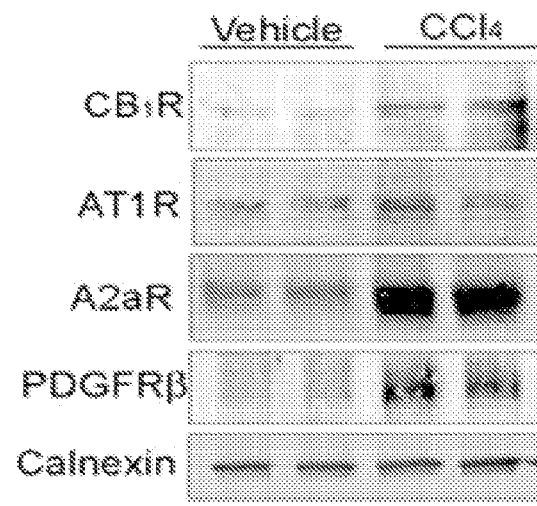

It was examined if $CB_1R$ interacts with AT1R and A2aR in vivo. Chronic treatment with $CCl_4$ lead to upregulation of $CB_1R$, A2aR, and to a lesser extent, of AT1R expression in mice liver (FIG. 1E). Co-immunoprecipitation experiments using livers from vehicle and $CCl_4$ treated mice showed that CB1R interacted with AT1R and with A2aR in fibrotic but not in control livers (FIG. 1F). Similarly CB1R was induced in human cirrhotic livers (FIG. 1G) and co-immunoprecipitation experiments showed that $CB_1R$ interacted with A2aR in human livers. Further, there was enhanced association of $CB_1R$ with AT1R and with A2aR in livers from cirrhotic patients as compared to control patients (FIG. 1H).

It was examined if, in the $CB_1R$-AT1R heteromer, AT1R signaling was affected by $CB_1R$. Angiotensin II (Ang II)-mediated mitogenic signaling was focused on because of the implication of this pathway in fibrosis[4,5]. Ang II treatment led to a marked enhancement of pERK levels in eHSCs compared to cHSCs. This increase in Ang II-mediated signaling was due to interactions with $CB_1R$ since treatment with a $CB_1R$ specific antagonist prevented Ang II-mediated ERK phosphorylation in eHSCs but not cHSCs (FIG. 2A). The role of endocannabinoids was further examined in AT1R signaling by blocking 2-arachidonoyl glycerol (2-AG) formation using the diacylglycerol lipase (DAGL) inhibitor tetrahydrolipstatin (THL). THL treatment decreased Ang II-mediated ERK phosphorylation in eHSCs, but not cHSCs (FIG. 2B). This, taken with the finding that $CB_1R$ antagonist blocked Ang II-mediated pERK indicated that in activated HSCs, Ang II-mediated signaling was controlled by endocannabinoid-dependent $CB_1R$ activity.

Similarly, it was found that the A2aR agonist-mediated enhancement of pERK levels was blocked by the $CB_1R$ antagonist (FIG. 2C). These results indicated that $CB_1R$ activity controlled the signaling and profibrogenic potential of at least two GPCRs involved in HSC activation and liver fibrosis.

Example 2

Characterization of the $CB_1R$-AT1R Complex and $CB_1R$ Regulates Ang-II Mediated Increase in pERK Materials and Methods Immunofluorescence and Confocal Microscopy Immunofluorescence and Confocal Microscopy was carried out as described (Rozenfeld and Devi, 2008). Slides were visualized with a Leica TCS SP5 confocal microscope. Images were acquired with an x63/1.32 PL APO objective lens, and analyzed in sequential scanning mode.

Generation of HEK293-Transfected Cells and Neuro2A Cell Line Stably Expressing AT1R. These cell lines were generated using standard procedure of transfection and antibiotic selection of expressing cells. Screening of positive cells was carried out by immunostaining of the receptors to evaluate the homogeneity of expression in the clones.

Western Blots and Immunoprecipitation Communoprecipitation and Western blotting—Cells were lysed for 1 h in lysis buffer (1% Triton, 150 mM NaCl, 1 mM EDTA, 1 mM EGTA, and 50 mM Tris-Cl, pH 7.4) containing protease inhibitor cocktail (Sigma). For immunoprecipitation, cell lysates containing 400-600 μg of protein was incubated with the anti-AT1R or anti-A2aR antibody/protein A/C agarose complex overnight at 4° C. The beads were washed three times with lysis buffer and once with the same buffer without detergent. Proteins were eluted in 60 μL of 2× Laemmli buffer containing 1% 2-mercaptoethanol. Proteins were resolved by 10% SDS-PAGE, and subjected to Western blotting as described (Rozenfeld and Devi, 2008). Western blot and phospho-ERK Assays were carried out as described in the case of experiments with Neuro2A cells (Rozenfeld and Devi, 2008). For experiments with HSCs, freshly plated cells were stimulated for 10 minutes with AngII in the presence or absence of SR141716 and THL (as indicated). Phospho ERK and ERK were detected with rabbit monoclonal anti-phospho-p44/42 MAPK (anti-pERK, 1:1000) and mouse monoclonal anti-p44/42 MAPK (anti-ERK, 1:1,000) antibodies. Both blotting and imaging with the Odyssey imaging system (LI-COR, Lincoln, Nebr.) were performed following the manufacturer's protocols. The secondary antibodies that were used included IRDye 680-labeled anti-rabbit antibody, IRDye 800-labeled anti-mouse and anti goat antibodies (1:10,000).

Results

Figure 3A:
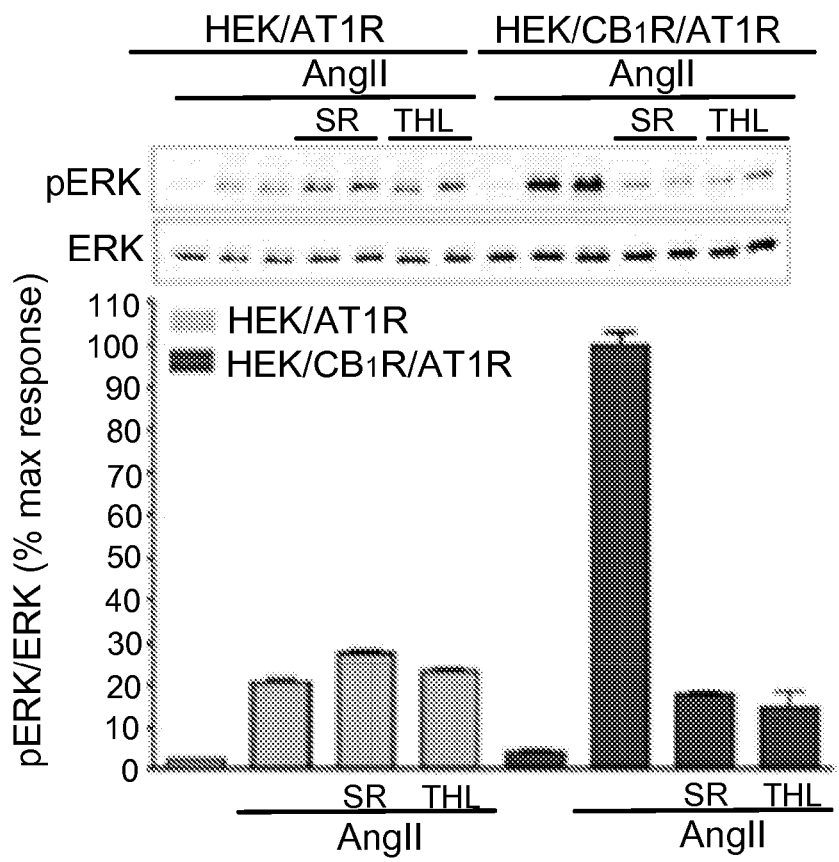
FIGS. 3A-3E. Characterization of the $CB_1R$-AT1R complex.

In order to clearly define the molecular mechanism underlying the functional interaction between $CB_1R$ and AT1R, recombinant systems were used. In transfected HEK293 cells, AT1R expressed alone was located at the plasma membrane, whereas $CB_1R$ was located in intracellular vesicles, as previously reported[6] (immunofluorescence data not shown). When co-expressed with AT1R, $CB_1R$ localized primarily to the plasma membrane along with AT1R (immunofluorescence data not shown). In these cells, stimulation with Ang II lead to a greater increase in pERK (as compared to cells expressing AT1R alone). Furthermore, in these cells, modulation of $CB_1R$ activity by the antagonist SR141716 (SR), or by inhibiting the endocannabinoid 2-AG production by the administration of THL, lead to a marked decrease in Ang II-mediated signaling (FIG. 3A). These results are in agreement with the results obtained in the eHSCs and show that irrespective of the cell system, $CB_1R$ affects AT1R properties in a similar fashion. Thus, the recombinant system is a useful model to explore the mechanisms of $CB_1R$-AT1R interactions.

Figure 3B:
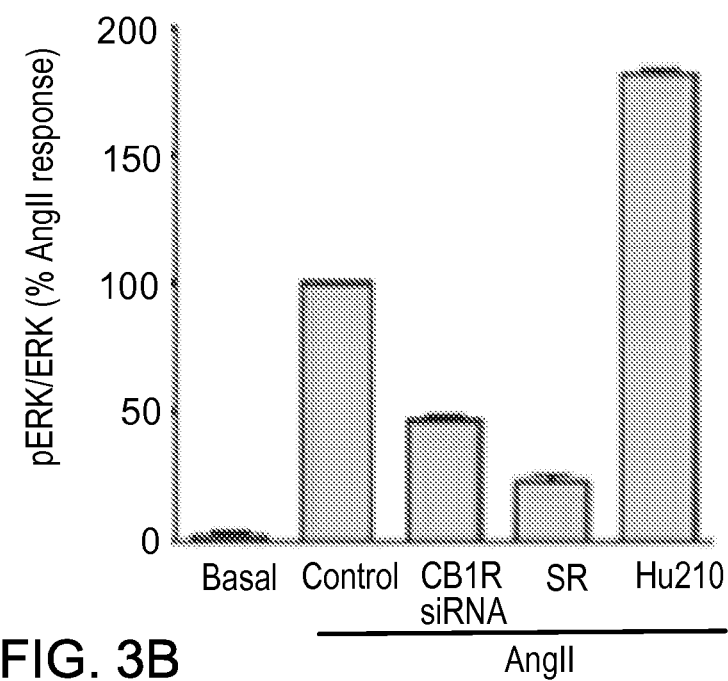
Figure 3C:
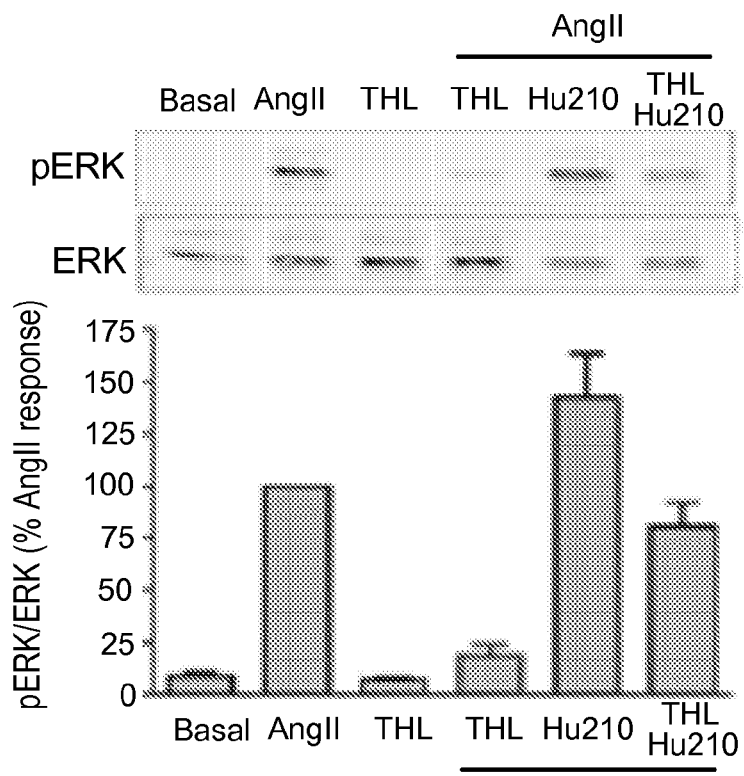
Figure 3D:
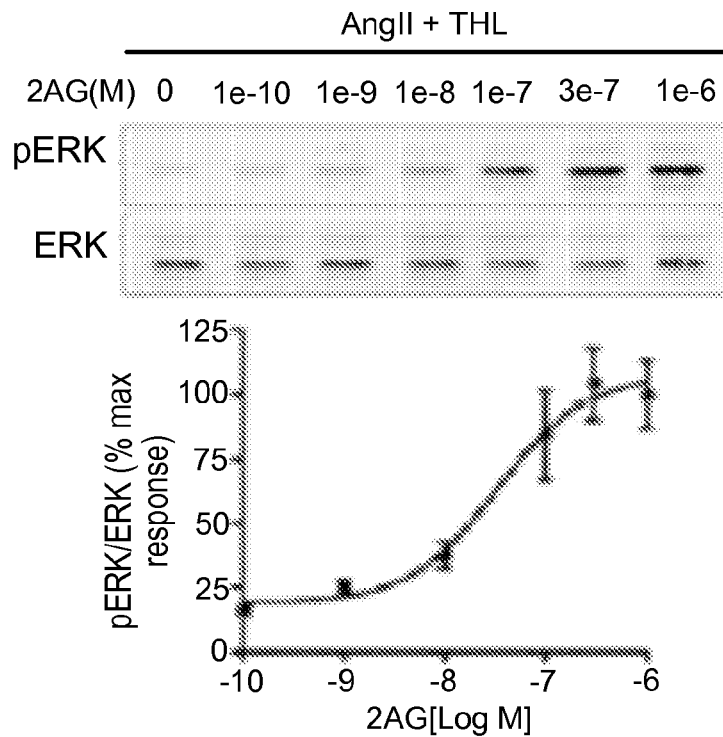
Figure 3E:
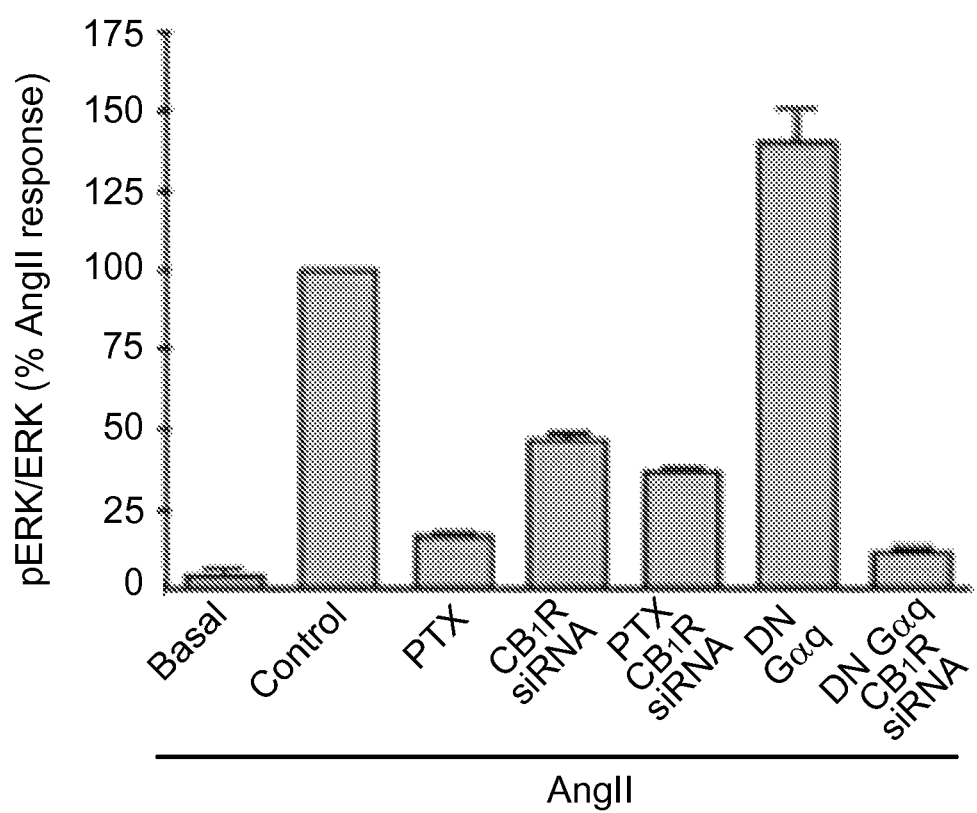
Figure 9A:
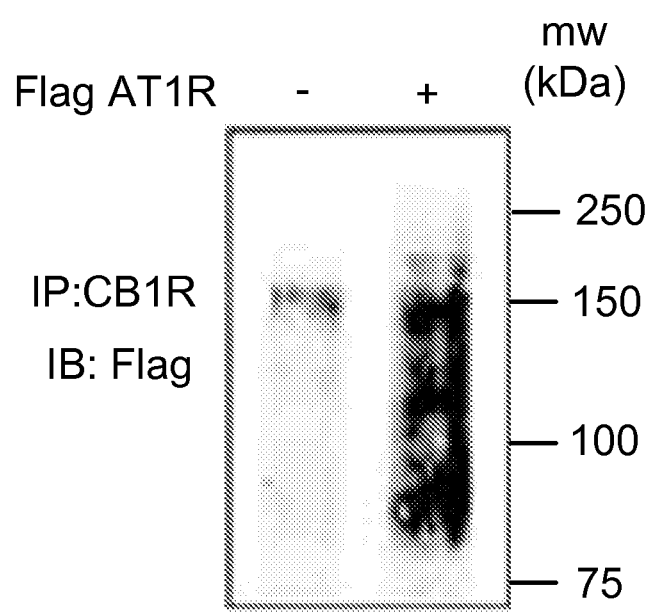
Figure 9D:
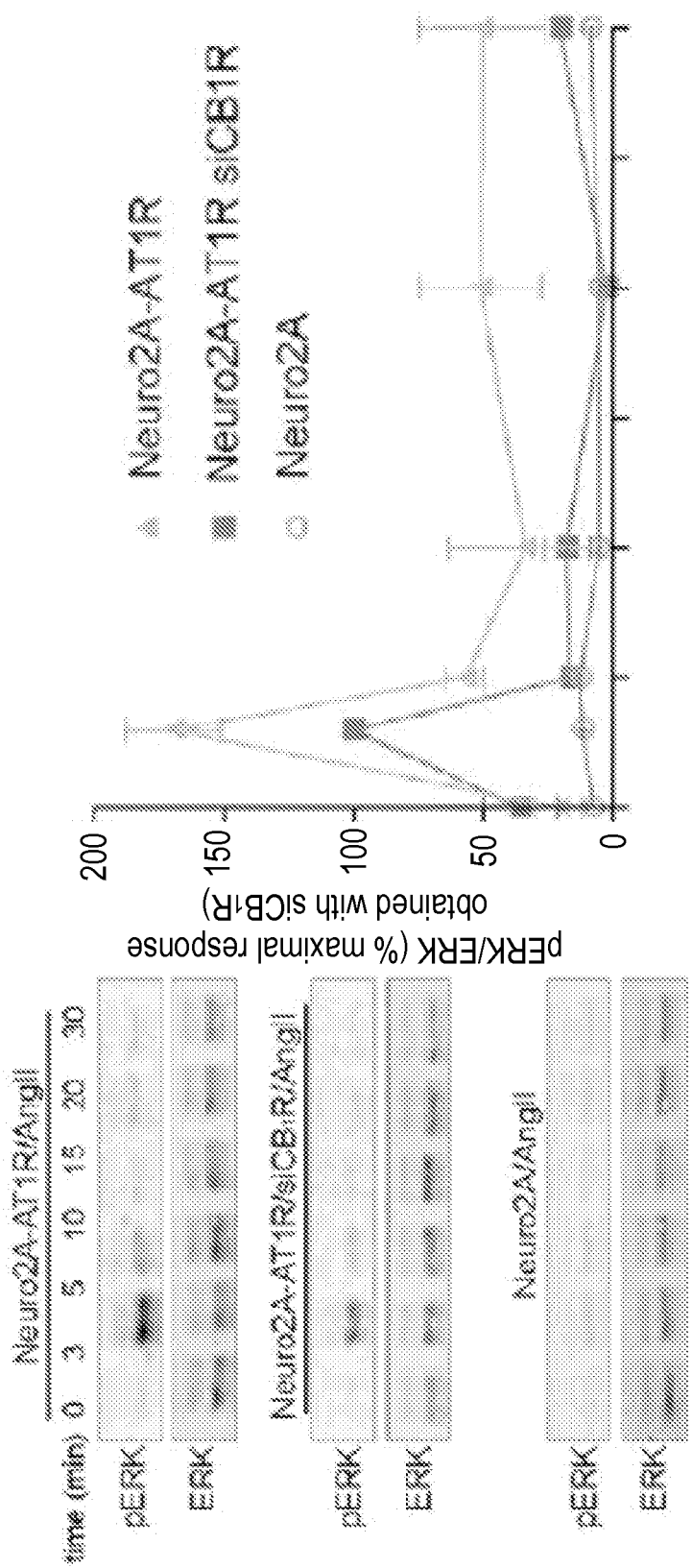
Figure 11A:
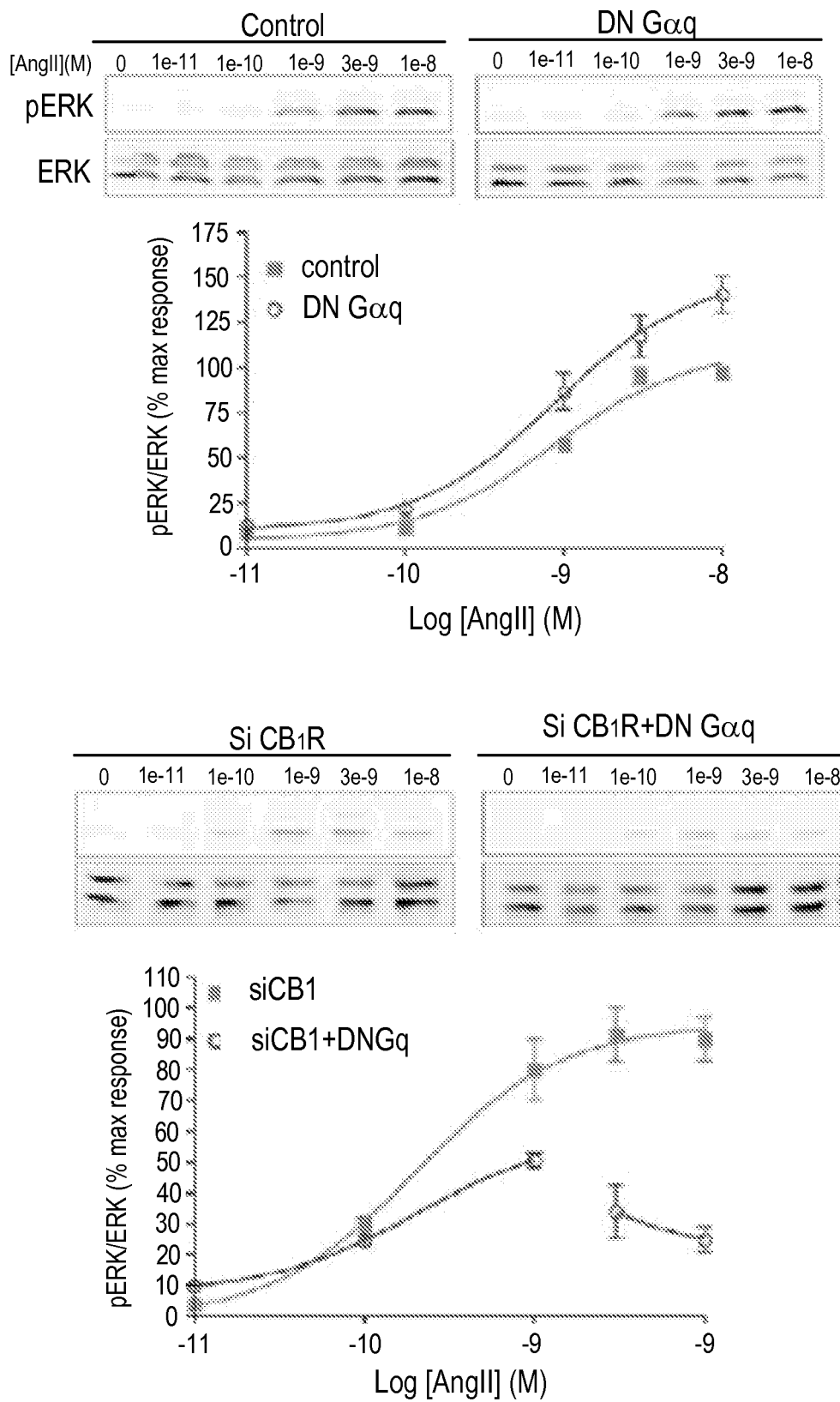
FIGS. 11A-11D: $CB_1R$ switches AT1R coupling to Gαi. Cells were stimulated with increasing concentration of Ang II. ERK phosphorylation was assessed by Western blot using antibodies to pERK and ERK. Data represent mean±SEM (n=3-5).
Figure 11B:
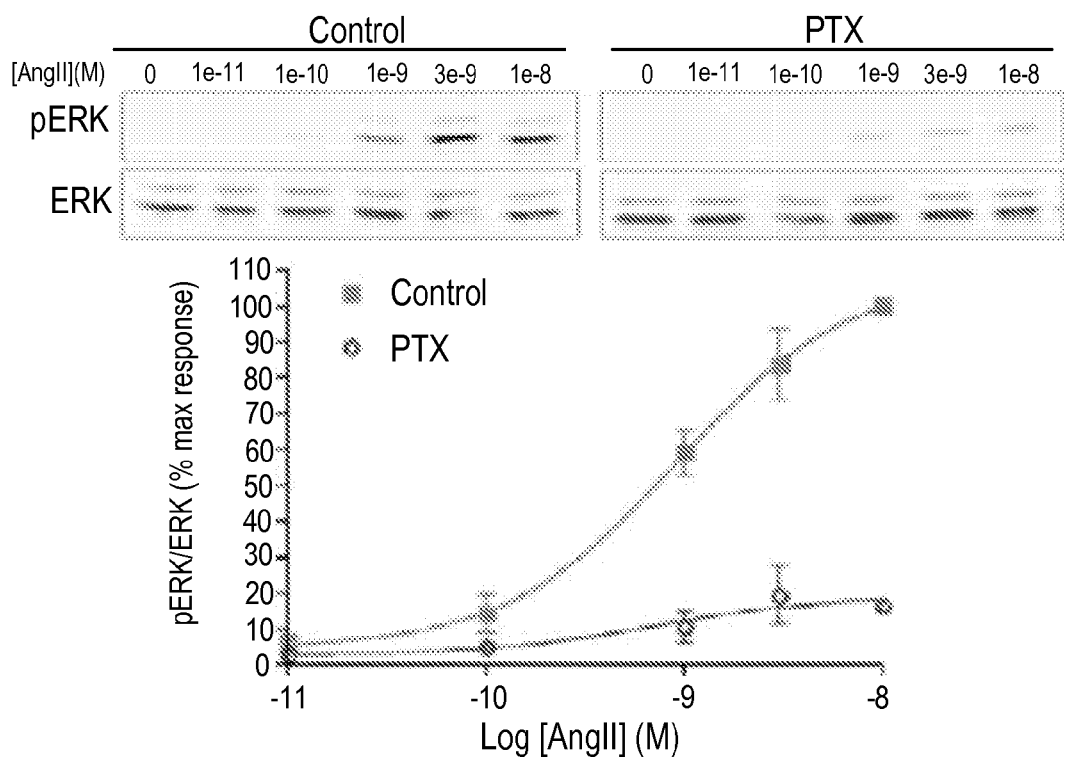
Figure 11B:
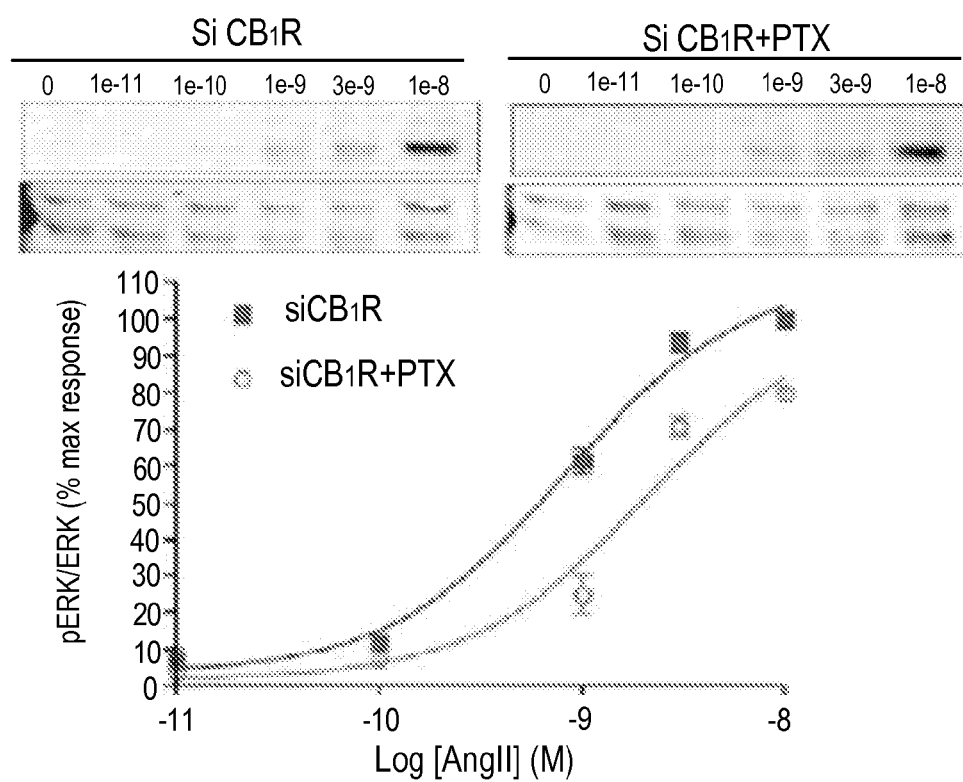
Figure 11C:
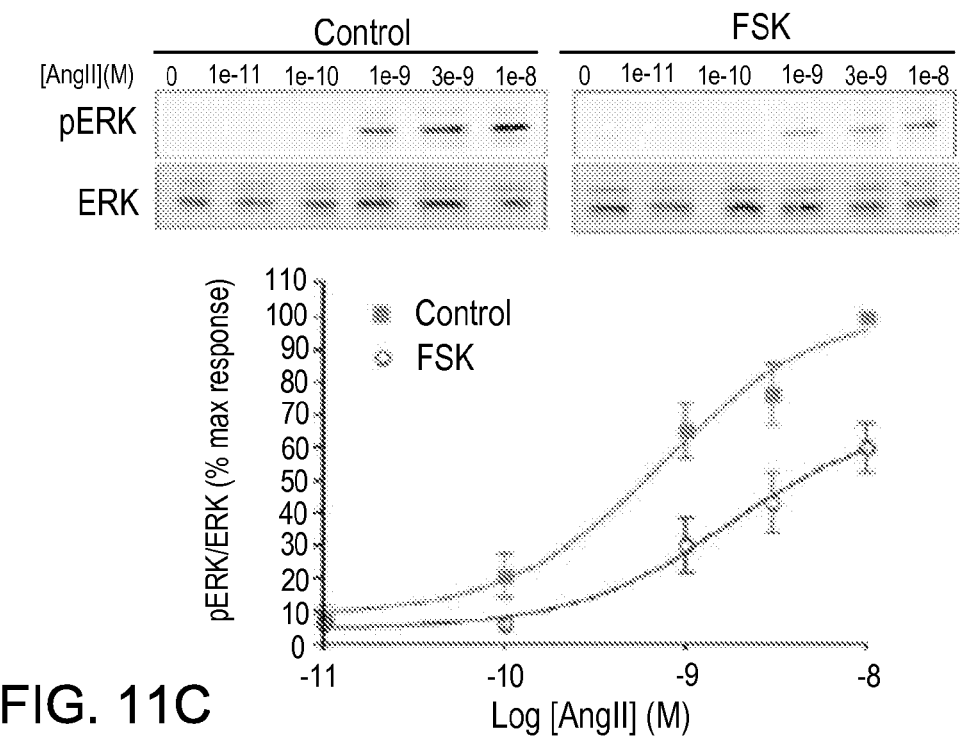
Figure 11D:
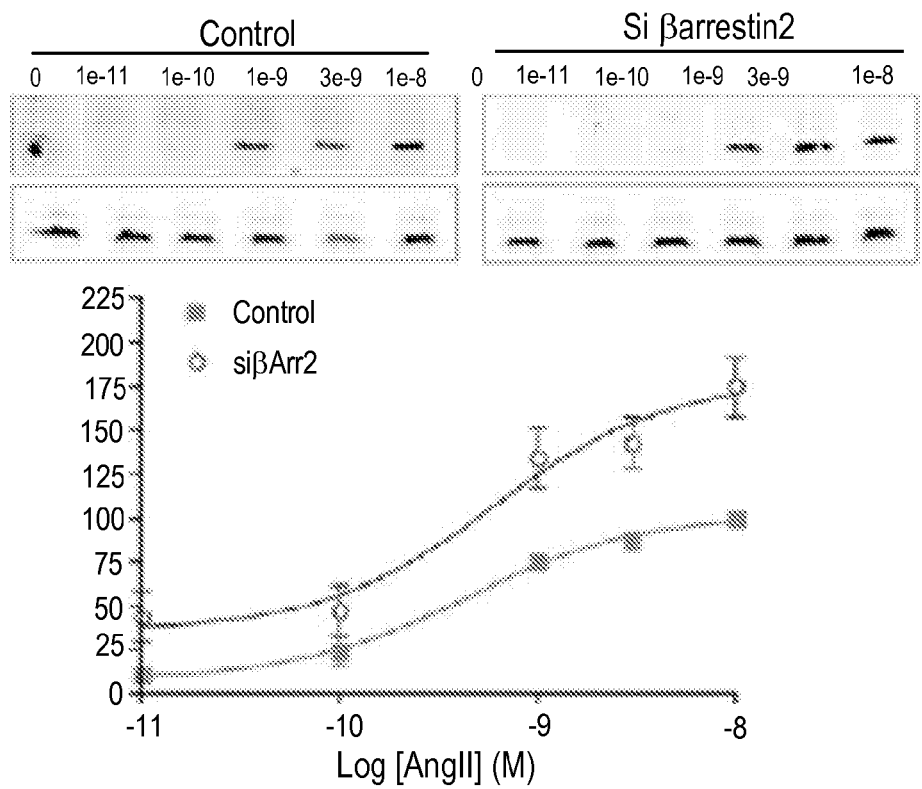

A neuroblastoma cell line (Neuro2A) that contained endogenous $CB_1R$ receptors was used, and a Neuro2A cell line was generated stably expressing AT1R. In these cells, $CB_1R$ and AT1R were colocalized and AT1R could be detected in $CB_1R$-immunoprecipitate, indicating the association of $CB_1R$-AT1R within a complex (immunofluorescence data not shown. Ang II stimulation lead to a dose-dependent rapid and transient enhancement of pERK levels (FIGS. 9A and 9B) and RNAi-mediated $CB_1R$ down-regulation lead to a dramatic decrease in this effect (FIG. 3B; FIGS. 9D & 10A), reminiscent of what was observed with cHSCs. Blocking $CB_1R$ using the specific antagonist SR141716 also blocked >80% of Ang II-mediated pERK (FIG. 2D; FIG. 10B). Blocking the production of the endocannabinoid 2-AG with THL lead to a loss of Ang II-mediated signaling (FIG. 2E); this was reversed by addition of Hu210 (a CB agonist, commercially available from Tocris Bioscience, Ellisville, Mo. 63021) or of exogenous 2-AG, (FIGS. 2E and H). These results, taken with the fact that stimulating $CB_1R$ with a non-signaling concentration of $CB_1R$ agonist potentiates AT1R signaling (FIG. 2F; FIG. 10C) confirm that AT1R signaling is controlled by $CB_1R$ activity in the context of the $CB_1R$-AT1R heteromer.

Example 3

$CB_1R$ Switches AT1R Coupling to $G\alpha i$

Materials and Methods

Dominant Negative $G\alpha q$ Construct

The construct is available at cDNA.org. Details are described below: The Q209L and D277N mutations were introduced into the human G protein alpha q subunit (GNA0Q00000) via the Quickchange mutagenesis kit (Stratagene). The mutations confer a preference for xanthine nucleotide binding. Insert size=1085 bp.

RNAi-mediated $CB_1R$ and βarrestin-2 downregulation. Plasmid and siRNA transfections were carried out as described (Rozenfeld and Devi, 2007 *FASEB J.* 2007 August; 21(10):2455-65).

Western Blots and Immunoprecipitation. Communoprecipitation and Western blotting—Cells were lysed for 1 h in lysis buffer (1% Triton, 150 mM NaCl, 1 mM EDTA, 1 mM EGTA, and 50 mM Tris-Cl, pH 7.4) containing protease inhibitor cocktail (Sigma). For immunoprecipitation, cell lysates containing 400-600 μg of protein was incubated with the anti-AT1R or anti-A2aR antibody/protein A/C agarose complex overnight at 4° C. The beads were washed three times with lysis buffer and once with the same buffer without detergent. Proteins were eluted in 60 μL of 2× Laemmli buffer containing 1% 2-mercaptoethanol. Proteins were resolved by 10% SDS-PAGE, and subjected to Western blotting as described (Rozenfeld and Devi, 2008). Western blot and phospho-ERK Assays were carried out as described in the case of experiments with Neuro2A cells (Rozenfeld and Devi, 2008). For experiments with HSCs, freshly plated cells were stimulated for 10 minutes with AngII in the presence or absence of SR141716 and THL (as indicated). Phospho ERK and ERK were detected with rabbit monoclonal anti-phospho-p44/42 MAPK (anti-pERK, 1:1000) and mouse monoclonal anti-p44/42 MAPK (anti-ERK, 1:1,000) antibodies. Both blotting and imaging with the Odyssey imaging system (LI-COR, Lincoln, Nebr.) were performed following the manufacturer's protocols. The secondary antibodies that were used included IRDye 680-labeled anti-rabbit antibody, IRDye 800-labeled anti-mouse and anti goat antibodies (1:10,000).

Results

Figure 12A:
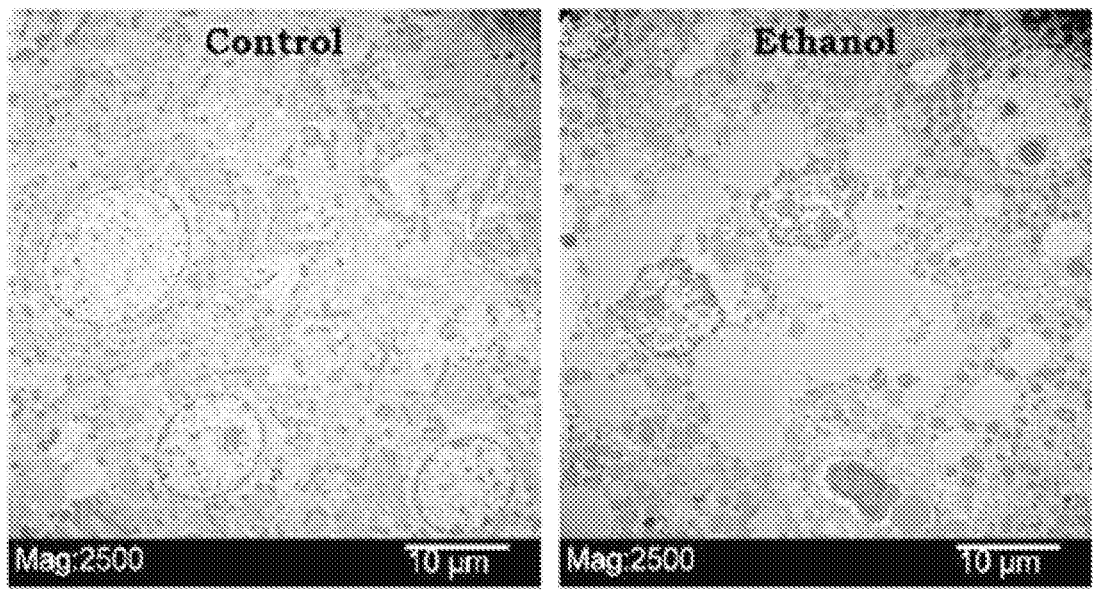
FIGS. 12A-12B. Preparation of the cHSC and eHSC isolated from alcohol fed rats. Rats (300 g female Sprague-Dawley, N=10/group) were fed the control or ethanol Lieber-DeCarli diets for 8 months.
Figure 12B:
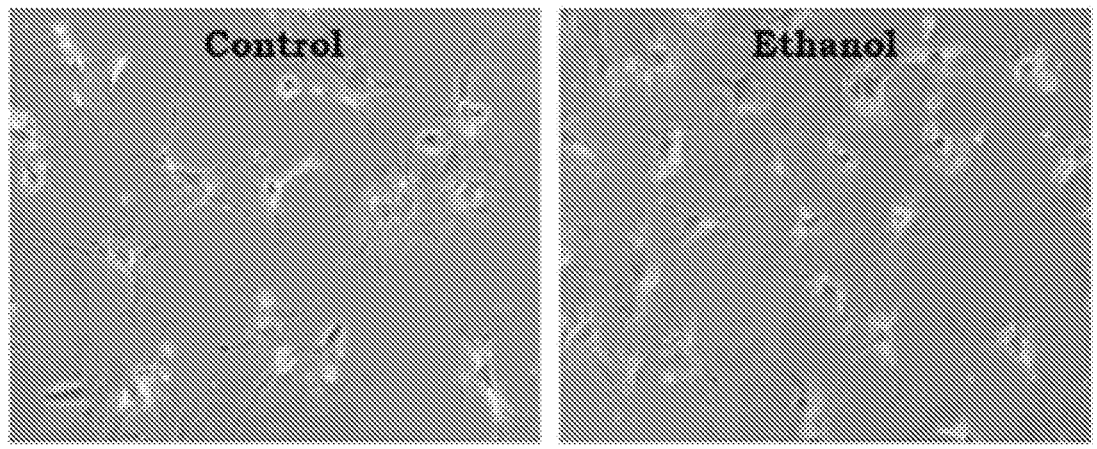

To delineate the novel pathway of the heteromer-mediated signaling, the nature of the G protein coupling to AT1R was investigated. Expression of a dominant negative $G\alpha q$ construct affected AT1R signaling only under conditions of $CB_1R$ down-regulation (FIG. 2F; FIG. 12A) indicating a loss of AT1R coupling to $G\alpha q$. Next, it was examined if there was a shift in coupling to $G\alpha i$. Treatment with pertussis toxin (PTX) (which blocks $G\alpha i$) markedly inhibited AT1R signaling in cells co-expressing $CB_1R$ and AT1R and this was reduced upon down-regulation of $CB_1R$ expression (achieved by RNAi) (FIG. 2I; FIG. 12B). It was also found that forskolin (Sigma-Aldrich, St. Louis, Mo. 63103) treatment (which interferes with $G\alpha i$-mediated signaling by preventing efficient inhibition of adenylyl cyclase) decreased AT1R-mediated signaling in the $CB_1R$-AT1R expressing cells (FIG. 12C), supporting a switch in G protein coupling facilitated by heteromerization. This switch in coupling of AT1R indicated a possible mechanism of G protein sequestration by the $G\alpha i$ coupled receptor $CB_1R$[7,8].

Finally, it was also found that heteromerization lead to changes in the nature of the interactions between AT1R and βarrestin-2. In contrast to the established contribution of βarrestin-2 in AT1R mitogenic signaling[9], it was found that down-regulation of βarrestin-2 (by RNAi) did not inhibit AT1R-mediated pERK in the $CB_1R$-AT1R expressing cells (FIG. 12D) confirming the change in the nature of coupling of AT1R by heteromerization with $CB_1R$.

Example 4

$CB_1R$ and A2aR Form a Complex in Activated HSCs, and $CB_1R$ Activity Controls A2aR-Mediated pERK Materials and Methods Western Blots and Immunoprecipitation. Communopre-cipitation and Western blotting—Cells were lysed for 1 h in lysis buffer (1% Triton, 150 mM NaCl, 1 mM EDTA, 1 mM EGTA, and 50 mM Tris-Cl, pH 7.4) containing protease inhibitor cocktail (Sigma). For immunoprecipitation, cell lysates containing 400-600 µg of protein was incubated with the anti-AT1R or anti-A2aR antibody/protein A/C agarose complex overnight at 4° C. The beads were washed three times with lysis buffer and once with the same buffer without detergent. Proteins were eluted in 60 µL of 2×Laemmli buffer containing 1% 2-mercaptoethanol. Proteins were resolved by 10% SDS-PAGE, and subjected to Western blotting as described (Rozenfeld and Devi, 2008). Western blot and phospho-ERK Assays were carried out as described in the case of experiments with Neuro2A cells (Rozenfeld and Devi, 2008). For experiments with HSCs, freshly plated cells were stimulated for 10 minutes with AngII (Tocris Bioscience, Ellisville, Mo. 63021) in the presence or absence of SR141716 (Tocris Bioscience, Ellisville, Mo. 63021) and THL (F. Hoffmann-La Roche Ltd, Basel, Switzerland) as indicated. Phospho ERK and ERK were detected with rabbit monoclonal anti-phospho-p44/42 MAPK (anti-pERK, 1:1000) and mouse monoclonal anti-p44/42 MAPK (anti-ERK, 1:1,000) antibodies. Both blotting and imaging with the Odyssey imaging system (LI-COR, Lincoln, Nebr.) were performed following the manufacturer's protocols. The secondary antibodies that were used included IRDye 680-labeled anti-rabbit antibody, IRDye 800-labeled anti-mouse and anti goat antibodies (1:10,000).

Results

In addition to $CB_1R$ and AT1R, several GPCRs have been shown to be involved in the development of fibrosis indicating that modulation of signaling by heteromerization with $CB_1R$ can be extended to other receptors. A2aR was focused on, since stimulation of this receptor activates mitogenic pathways leading to the expression of fibrosis markers[3,10]. A2aR is constitutively expressed in HSCs, displaying only a slight increase in its levels (~15%) in activated HSCs (FIG. 1C). In these cells, A2aR associates with $CB_1R$ since co-immunoprecipitation leads to the isolation of the two receptors in an interacting complex (FIG. 1D). More importantly, the A2aR agonist-mediated enhancement of pERK levels (via the A2aR agonist CGS21680 (Tocris Bioscience, Ellisville, Mo. 63021) is blocked by the $CB_1R$ antagonist SR141716 (SR) (Tocris Bioscience, Ellisville, Mo. 63021) (FIG. 3A).

These results indicated that $CB_1R$ activity controls the signaling and profibrogenic potential of at least two GPCRs involved in HSC activation and liver fibrosis.

Example 5

$CB_1R$ Antagonist Prevents Ang II-Mediated Fibrogenic Response in eHSCs

Materials and Methods

Reverse Transcription and Real-Time PCR. Total RNA was isolated from 3×10⁸ HSCs using the TRIzol method (Invitrogen, Carlsbad, Calif., USA). RNA (1.0 µg) was reverse-transcribed in 20 µl of buffer containing 50 µM oligo (dT)20, 25 mM $MgCl_2$, 0.1 M dithiothreitol, 40 U/µl RNase-OUT, and 200 U/µl SuperScript III RT for 50 min at 50° C. The reaction was stopped by incubating the samples at 85° C. for 5 min, and 40 µl of nuclease-free water was added. Real-time PCR was performed by using the Brilliant SYBR Green QPCR Master Mix. The PCR template source was either 30 ng of first-strand cDNA or purified DNA standard. Primer sequences used to amplify the desired cDNA are detailed in Table 2. Amplification was performed with a spectrofluorometric thermal cycler (Stratagene). After an initial denaturation step at 95° C. for 10 min, amplification was performed using 40 cycles of denaturation (95° C. for 30 s), annealing (56° C. for 1 min), and extension (72° C. for 1 min). To standardize mRNA levels, we amplified GAPDH, a housekeeping gene, as an internal control. Gene expression was normalized by calculating the ratio between the number of cDNA copies of collagen type I, type III, TGF-β, α-SMA and that of GAPDH. For analysis of gene expression, after reverse transcription, the number of copies of mRNA for the indicated transcripts were determined by real-time PCR. Data were normalized to GAPDH mRNA and are expressed as the mean±SD (n=3 in quadruplicate).

$CB_1R$ antagonists. SR141716: eHSCs were stimulated with Ang II in the absence or presence of SR141716 (SR; Tocris Bioscience, Ellisville, Mo. 63021) for 4 hours before the RNA was harvested.

CGS21680 (CGS)— eHSCs were stimulated with CGS (Tocris Bioscience, Ellisville, Mo. 63021) in the absence or presence of SR for 6 hours before the RNA was harvested. In order to determine the CGS-mediated fibrogenic response in mouse fibrotic liver, $CCl_4$- or vehicle-treated mice were injected intraperitoneally (i.p.) with vehicle, CGS, or CGS+AM 251 (AM, $CB_1R$ antagonist). After 6 hours, the mice were sacrificed, their liver quickly removed and the RNA harvested.

Results

Figure 4A:
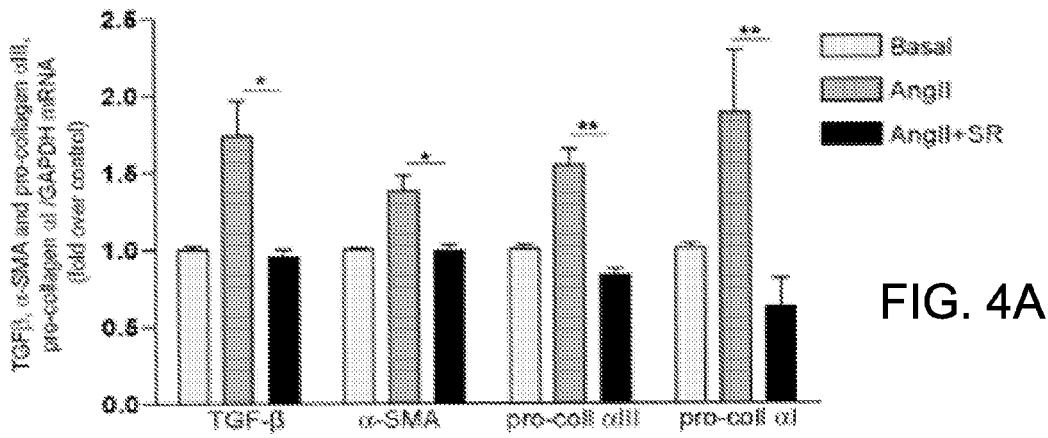
FIGS. 4A-4C. $CB_1R$ controls the profibrogenic activity of AT1R and A2aR. For analysis of gene expression, after reverse transcription, the number of copies of mRNA for the indicated transcripts were determined by real-time PCR. Data were normalized to GAPDH mRNA and are expressed as the mean±SD (n=3 in quadruplicate).
Figure 4B:
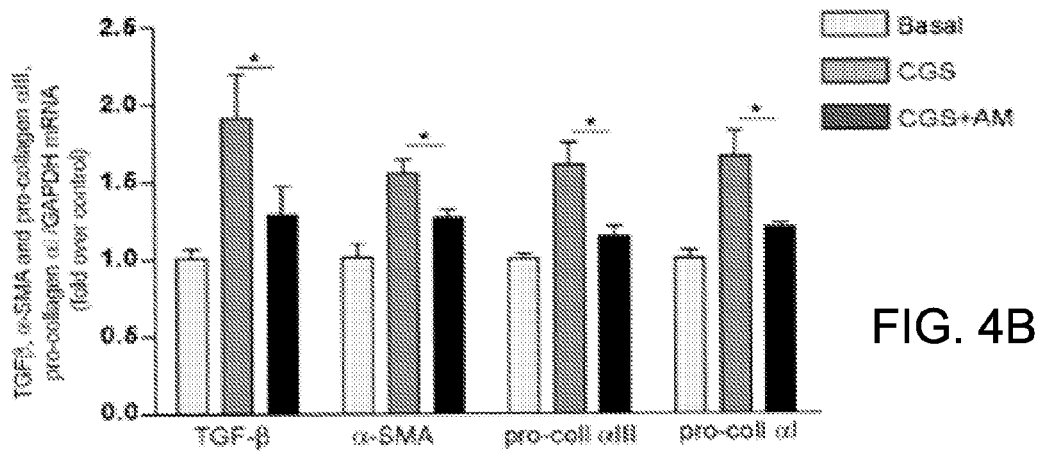

The role of $CB_1R$ complexes were explored in the regulation of the expression of profibrogenic markers in liver fibrosis. It was found that stimulation of AT1R or A2aR leads to an increase in expression of α-SMA, TGFβ, pro-collagen α III and pro-collagen α I by as much as 120-160% over baseline in activated HSCs; this increase can be completely blocked by concomitant treatment with the $CB_1R$ antagonist (FIGS. 4A and 4B) indicating that the profibrogenic potential of these receptors is under the control of $CB_1R$ activity.

Example 6

Anti-$CB_1R$/AT1R Heteromer Monoclonal Antibody

Materials and Methods

A subtractive immunization strategy was used to generate antibodies that selectively recognize the endogenous $CB_1R$/AT1R heteromer but do not recognize either the $CB_1R$ or AT1R receptors alone. Mice were first made tolerant to unwanted epitopes on membrane proteins by the simultaneous administration of Neuro2A cell membranes (which endogenously express $CB_1R$ and cyclophosphamide).

Subtractive Immunization: For induction of tolerance to immunogenic epitopes in HEK-293 membranes, female balb/c mice (6-8 weeks old, 25-35 g body weight) were injected intraperitoneally (i.p.) with 5 mg Neuro-2A membranes and 15 min later with cyclophosphamide (100 mg/kg body weight, i.p.). The cyclophosphamide injection was repeated after 24 and 48 h respectively. Mice were bled every 15 days and antibody titers checked by ELISA against Neuro-2A membranes. This protocol was repeated at 2 week intervals until stable background titers were obtained with Neuro-2A membranes. Mice were then given an i.p. injection of membranes from Neuro-2A cells expressing AT1 angiotensin receptors (5 mg) in complete Freund's adjuvant. Booster i.p. injections of Neuro-2A cells expressing AT1 angiotensin receptors were administered every 15 days. Antibody titers were checked by ELISA against Neuro2A membranes from untransfected cells and from cells expressing AT1 receptors. Spleens from animals giving a high titer with Neuro-2A cells expressing AT1 angiotensin receptors were fused with SP-20 myeloma cells to generate monoclonal antibodies as described (Gupta et al., *JBC* 282:5116, 2007). Clones secreting monoclonal antibodies were screened by ELISA against untransfected Neuro-2A membranes, and Neuro-2A cells expressing AT1 angiotensin receptors using 1:10 hybridoma supernatant and 1:500 horse radish peroxidase labeled anti-mouse IgG. Hybridoma supernatant from positive clones was concentrated using Centricon 10 and stored at a concentration of 10 μg protein/μl.

This results in the destruction of antibody-generating activated B cells. Once a low titer to Neuro-2A membrane proteins was achieved [Gupta et al., *J Biol. Chem.* 2007 Dec. 21; 282(51):36797-807], mice were immunized with Neuro-2A membranes expressing AT1R receptors [Gomes et al., *Methods Mol. Med.* 84:157, 2003].

The antibody titer was monitored after booster injections and once a high titer was obtained, the spleens of these mice were used to generate monoclonal antibodies (mAbs).

Results

TABLE 1

Number of clones expressing CB1-AT1 heteromer specific antibodies.

| Positive Titer | CB1-AT1 | AT1 | CB1 |
| --- | --- | --- | --- |
| Between 2-3 | 1 | zero | zero |
| Between 1-2 | 18 | zero | 1 |
| Between 0.5-1 | 31 | 5 | 1 |

The supernatants from the hybridoma clones were screened with Neuro-2A membranes alone, membranes from cells expressing only AT1 receptors, and membranes from cells co-expressing both $CB_1R$ and AT1R receptors. This led to the identification of a number of antibody-secreting clones that gave a high titer with membranes co-expressing $CB_1R$-AT1R receptors [Gupta et al., *JBC* 282:5116, 2007].

The specificity of the AT1R-CB1R antibody for cells expressing AT1R and CB1R, but not for cells expressing either of these receptors alone is demonstrated by results shown in FIGS. 8A-E. AT1R-CB1R antibody was tested for binding of AT1R-CB1R in Neuro2A, Neuro2A-AT1R, and Neuro2A-AT1R in which CB1R expression was downregulated by RNAi using an enzyme-linked immunoabsorbent assay (ELISA). ELISA assay indicated the presence of a specific AT1R-CB1R epitope detected only in Neuro2A-AT1R (FIG. 8A). AT1R-CB1R antibody was screened against membranes from HEK293 cells coexpressing AT1R and CB1R, or membranes from cells expressing only AT1R or CB1R. ELISA assay indicated the presence of a specific AT1R-CB1R epitope detected only in AT1R-CB1R expressing cells (FIG. 8B). There was no signal with membranes from cells coexpressing CB1R with CB2R, DOR, MOR or KOR, or cells expressing DOR with KOR or MOR (FIG. 8C).

The specificity of the antibody was further characterized using cells that expressed different ratios of CB1R and AT1R. Maximal recognition by the heteromer antibody was observed when CB1R and AT1R were expressed at similar levels, but not when expressed at 1:5 or 5:1 ratios) (FIG. 8D). AT1R-CB1R was also used to measure the AT1R-CB1R immunoreactivity from activated (eHSCs) and control (cHSCs) hepatic stellate cells. ELISA assay indicated the presence of a specific AT1R-CB1R epitope detected only in activated but not in quiescent HSCs (FIG. 8E).

Figure 8F:
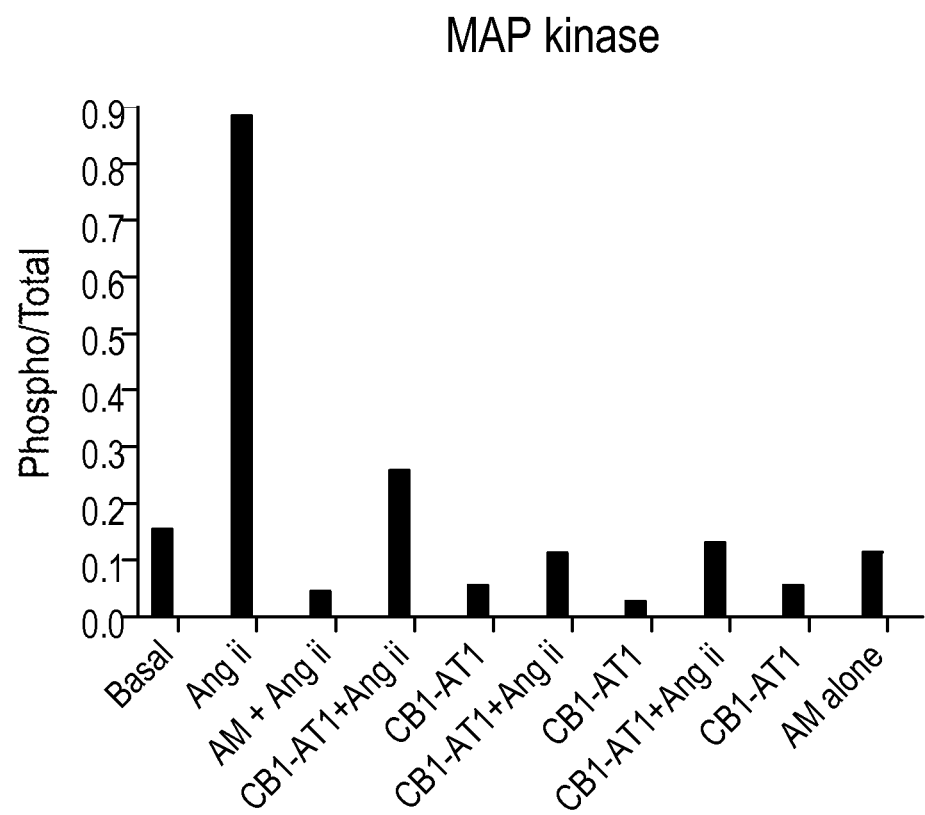
Figure 8G:
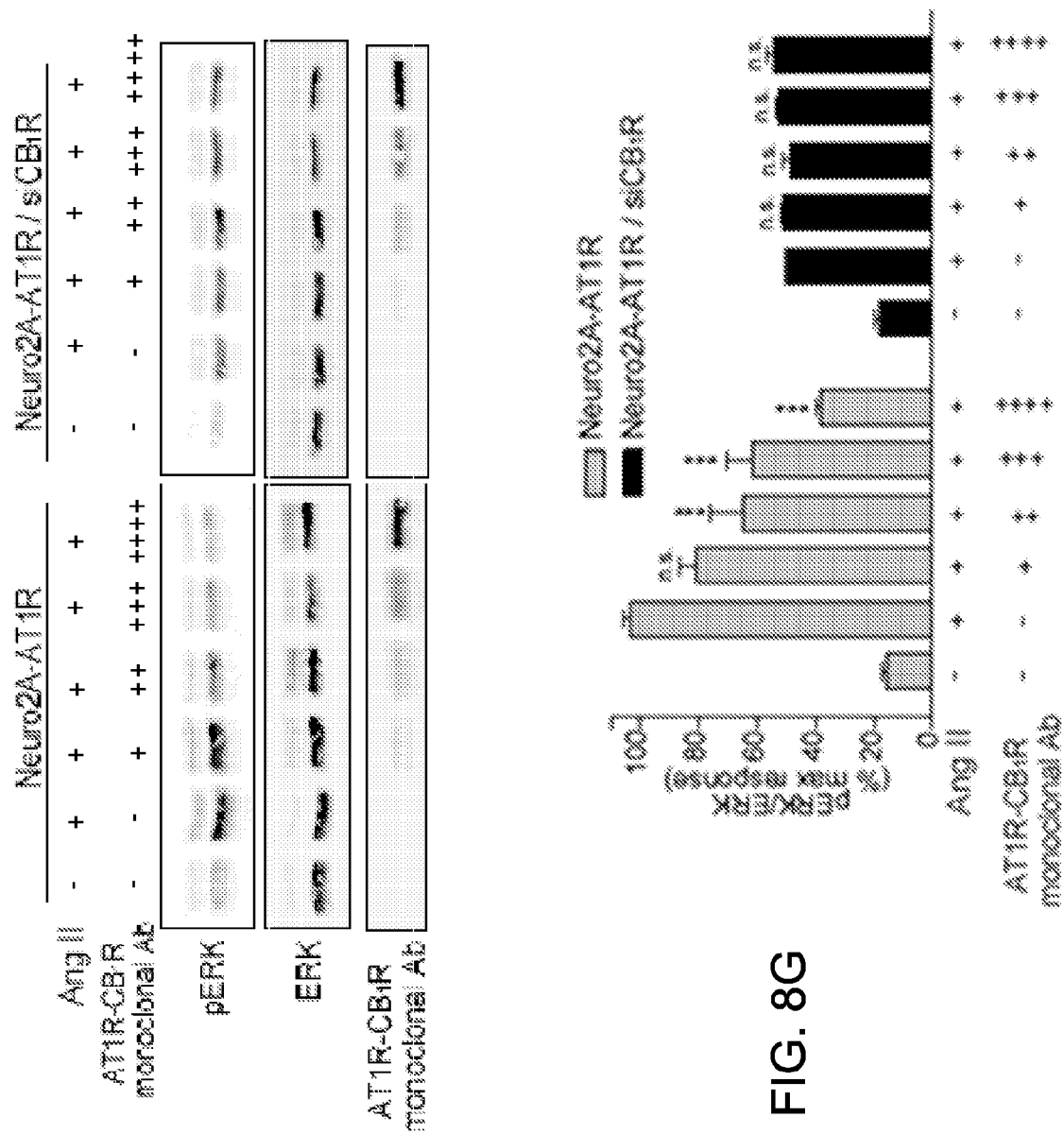

The ability of the heteromer-specific monoclonal antibody to selectively inhibit signaling by $CB_1R$-AT1R heteromers was examined. CB1R-AT1R mediated activity was selectively blocked by heteromer specific antibody. Heteromer-selective antibody significantly blocked AT1R activity mediated increases in ERK phosphorylation (FIGS. 8F and 8G). These results demonstrate that the monoclonal antibody against the AT1R-CB1R heteromer blocks receptor signaling only in the context of the heteromer but not when the receptors are expressed alone.

Example 7

$CB_1R$ Activity Controls Other GPCR-Mediated Pro-Fibrogenic Gene Expression and Properties in Animal Models of Fibrosis Materials and Methods Murine model of liver fibrosis and human tissues. Wild-type C54bl6 mice were treated with i.p. injections of $CCl_4$ (2 mL/kg CCl4 mixed with mineral oil; 10% v/v) or mineral oil, 3 times a week for 8 weeks (n=5-6 per group). There were no deaths in any of the groups. 48 hours after the last $CCl_4$ injection, mice were injected i.p. with vehicle (DMSO 4% in saline), CGS21680 (2 mg/kg) or AM251 (Tocris Bioscience, Ellisville, Mo. 63021) (2 mg/kg)+CGS21680. Six hours after the injections, mice were sacrificed by CO2 narcosis. Aliquots of liver tissue (50-100 mg) were flash frozen and kept at −80° C. until RNA isolation. The tissue was minced and homogenized in TRIzol reagent, and RNA was extracted according to the manufacturer's instructions and then dissolved in sterile DEPC water and stored at −80° C. RT-PCR was performed as described:

Real-Time Quantitative Reverse Transcription-Polymerase Chain Reaction. Total RNA was isolated from $3 \times 10^8$ HSCs using the TRIzol method (Invitrogen, Carlsbad, Calif., USA). RNA (1.0 μg) was reverse-transcribed in 20 μl of buffer containing 50 μM oligo(dT)20, mM $MgCl_2$, 0.1 M dithiothreitol, 40 U/μl RNaseOUT, and 200 U/μl SuperScript III RT for 50 min at 50° C. The reaction was stopped by incubating the samples at 85° C. for 5 min, and 40 μl of nuclease-free water was added. Real-time PCR was performed by using the Brilliant SYBR Green QPCR Master Mix. The PCR template source was either 30 ng of first-strand cDNA or purified DNA standard. Primer sequences used to amplify the desired cDNA are detailed in Table 2. Amplification was performed with a spectrofluorometric thermal cycler (Stratagene). After an initial denaturation step at 95° C. for 10 min, amplification was performed using 40 cycles of denaturation (95° C. for 30 s), annealing (56° C. for 1 min), and extension (72° C. for 1 min). To standardize mRNA levels, GAPDH, a housekeeping gene, was amplified as an internal control. Gene expression was normalized by calculating the ratio between the number of cDNA copies of TGF-β and α-SMA and that of GAPDH.

TABLE 2

| Collagen (α1) (I) | Sense 5' CGA CTA AGT TGG AGG GAA CGG TC 3' (SEQ ID NO: 1) | 319 |
| --- | --- | --- |
| | Antisense 5' TGG CAT GTT GCT AGG CAC GAC 3' (SEQ ID NO: 2) | |

TABLE 2-continued

| | | |
|---|---|---|
| Collagen (α1) (III) | Sense 5' CGA GGT GAC AGA GGT GAA AGA 3' (SEQ ID NO: 3)<br>Antisense 5' AAC CCA GTA TTC TCC GCT CTT 3' (SEQ ID NO: 4) | 336 |
| TGF-β1 | Sense 5' TAT AGC AAC AAT TCC TGG CG 3' (SEQ ID NO: 5)<br>Antisense 5' TGC TGT CAC AAG AGC AGT G 3' (SEQ ID NO: 6) | 162 |
| GAPDH | Sense 5' TGT GTC TGT CGT GGA TCT GA 3' (SEQ ID NO: 7)<br>Antisense 5' CCT GCT TCA CCA CCT TCT TGA 3' (SEQ ID NO: 8) | 76 |
| α-SMA | Sense: TCC TCC CTG GAG AAG AGC TAC (SEQ ID NO: 9)<br>Antisense: TAT AGG TGG TTT CGT GGA TGC (SEQ ID NO: 10) | |

Results

Figure 4C:
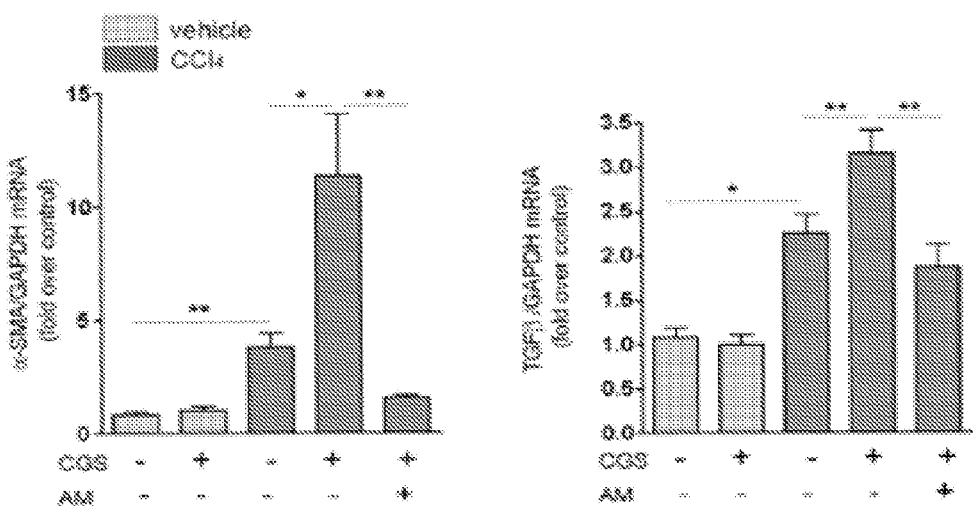

In livers from $CCl_4$ treated mice, upregulated expression of profibrogenic genes was further increased by acute injection with the A2aR agonist CGS (FIG. 4C). Co-administration of the CB1R antagonist AM251 with CGS prevented CGS-induced profibrogenic gene expression. CGS treatment did not elevate the expression of profibrogenic genes in non-fibrotic mouse livers (from vehicle-treated mice), supporting the notion that A2aR exhibits profibrogenic properties only in fibrotic livers. The study herein study shows that specific changes occurring in activated HSCs, such as $CB_1R$ upregulation can cause A2aR to be profibrogenic. Altogether, these results indicate that in activated HSCs, $CB_1R$ activity controls other GPCR-mediated profibrogenic gene expression and properties, and this can be observed in vivo, in animal models of liver fibrosis.

Example 8

Chronic Alcohol Feeding Model

Materials and Methods

Rats (300 g female Sprague-Dawley, N=10/group) were fed the control or ethanol Lieber-DeCarli diets for 8 months (See Lieber C S, DeCarli L M. Liquid diet technique of ethanol administration: 1989 update. *Alcohol Alcohol* 1989; 24: 197-211). Animals received human care according to the criteria outlined in the Guide for Care and Use of Laboratory Animals. ALT, AST, ethanol, and non-esterified fatty acids were assayed using kits from Thermo Electron Corporation (Waltham, Mass.), Sigma (St. Louis, Mo.), and Wako Chemicals (Richmond, Va.), respectively. H&E staining and TEM sections were prepared according to standard methodology and evaluated by a liver pathologist.

Details regarding pathology of the liver of the control and alcohol fed rats are available. See, Cubero F J, Nieto N. Ethanol and arachidonic acid synergize to activate Kupffer cells and modulate the fibrogenic response via tumor necrosis factor alpha, reduced glutathione, and transforming growth factor beta-dependent mechanisms; *Hepatology.* 2008 December; 48(6):2027-39; Urtasun R, Cubero F J, Vera M, Nieto N. Reactive nitrogen species switch on early extracellular matrix remodeling via induction of MMP1 and TNFalpha. *Gastroenterology.* 2009; 136: 1410-22.

Results

Ultrastructural analysis depicting micro- and macrovesicular steatosis, vacuolization, and electron dense mitochondria in livers from ethanol fed rats (FIG. 12A, right) compared to livers from control rats (FIG. 12A, left) (magnification=2500×). FIG. 12B shows light micrographs from HSC isolated from control and ethanol-fed rats. Details regarding pathology of the liver of the control and alcohol fed rats are described in (Cubero and Nieto, 2008; Urtasun et al., 2009). Briefly, Hematoxylin and eosin staining showed microvesicular and macrovesicular steatosis in livers from ethanol-fed rats; and transaminases and nonesterified fatty acids were elevated twofold and sixfold respectively, in the ethanol-fed rats.

Example 9

Methods of Screening for DAG Lipase Inhibitors

Materials and Methods

Neuro2A cells expressing endogenous $CB_1R$ and recombinant AT1R were pretreated with vehicle or THL (2 μM) for 3 hours in serum free media and stimulated with vehicle (CTL=control) or with the receptor ligand (angiotensin II) for 3 minutes. Cells were lysed and the cell lysates were probed for the levels of pERK1/2 and ERK1/2 by Western blot, using anti ERK and pERK from Cell Signaling Technology (Danvers, Mass. 01923). To assess the effect of THL on Ang II-mediated ERK phosphorylation in Neuro2A-AT1 cells, cells were pretreated with THL (1 μM) for two hours, then they were stimulated with 10 nM Ang II in the presence or absence of 2-AG (100 nM), for 3 minutes. ERK phosphorylation was assessed by Western blot using antibodies to pERK and ERK (n=3-5). To set up a high throughput screening assay, 24 h after plating, the cells were starved for 2 hours, then incubated with vehicle (DMSO) or with THL (1 μM) for 2 hours, then stimulated with Ang II (10 nM) for 3 minutes. The cells were processed for infrared detection of pERK.

Results

Figure 5:
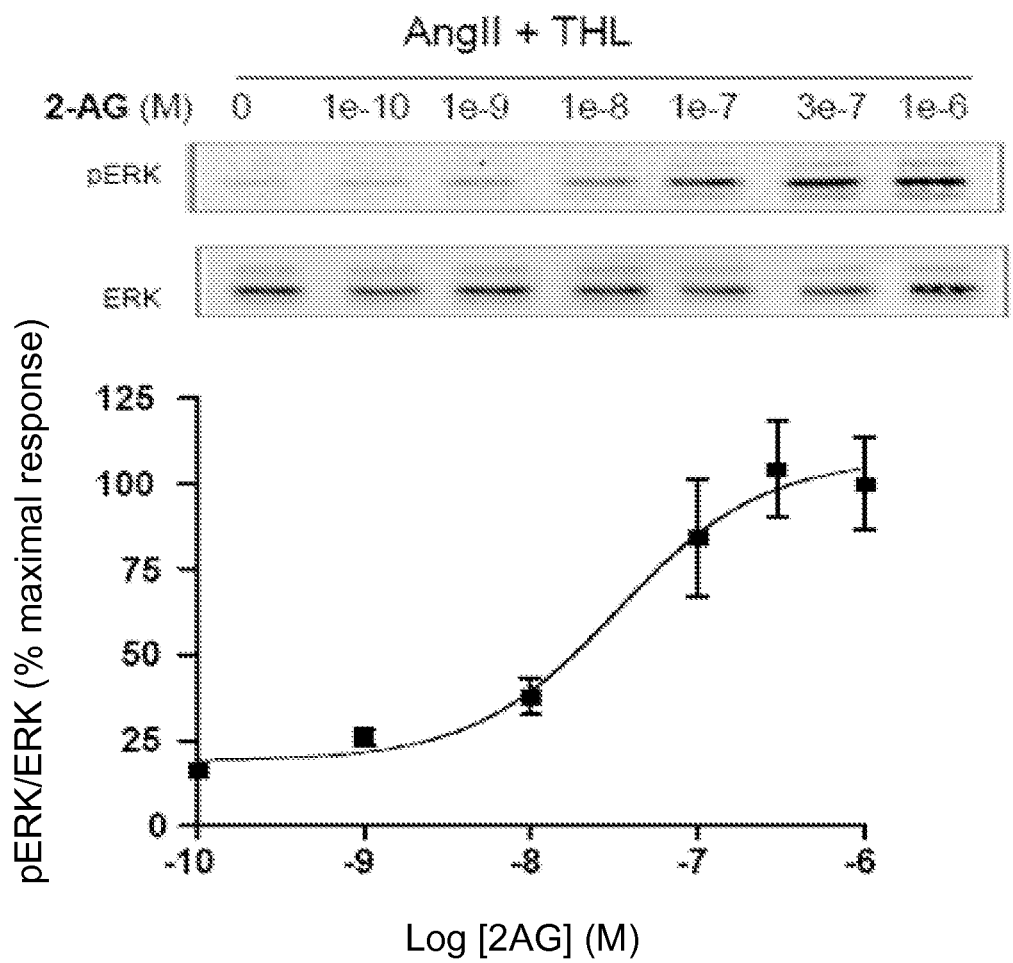
FIG. 5. Phospho-ERK expression following treatment with THL and 2-AG. Neuro2A-AT1 were pre-treated with THL (2 μM, 3 h) in serum free media and stimulated with increasing concentrations of 2-AG in the presence of Ang II for 3 minutes. Cells were lysed, and cell lysates were probed for the levels of pERK1/2 and ERK 1/2.

A receptor complex system was set up involving dimerization of $CB_1R$ with AT1R. This system exhibits the unique property that neither $CB_1R$ nor the associated receptor (AT1R) is able to signal through the ERK1/2 pathway upon stimulation with its cognate agonist. However, co-stimulation with a combination of the agonists for both receptors leads to ERK1/2 phosphorylation Inhibition of the production of 2-AG using the lipase inhibitor THL prevents 2-AG-mediated basal stimulation of $CB_1R$. In these conditions, there is a marked decrease in ERK1/2 phosphorylation upon agonist stimulation of the associated receptor (FIG. 5).

Figure 6:
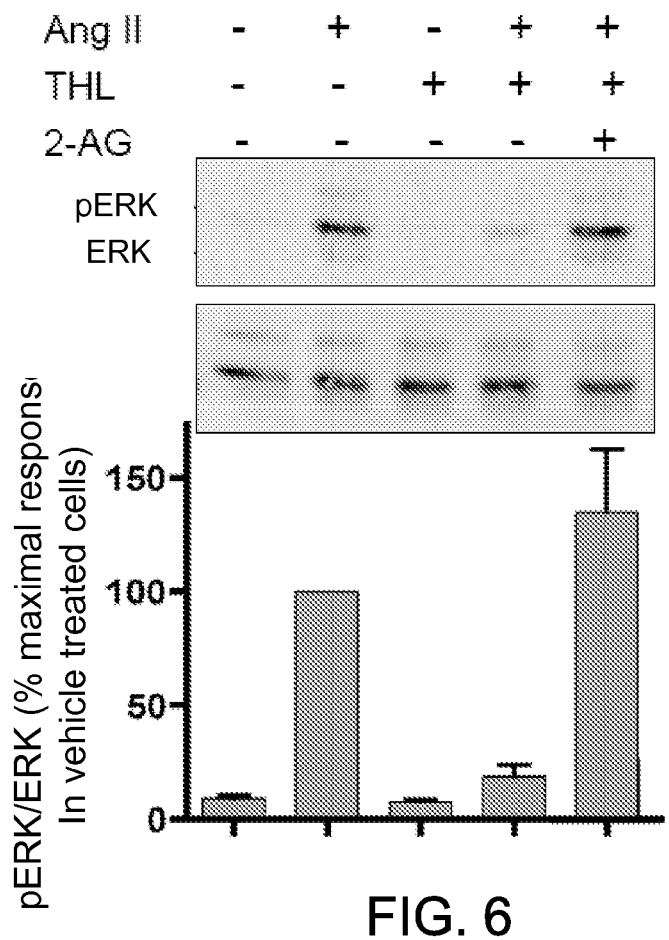
FIG. 6. Effect of THL on Ang II-mediated ERK phosphorylation in Neuro2A-AT1 cells. Cells were pretreated with THL (1 μM) for two hours, then they were stimulated with 10 nM Ang II in the presence or absence of 2-AG (100 nM), for 3 minutes. ERK phosphorylation was assessed by Western blot using antibodies to pERK and ERK. N=3-5.
Figure 7:
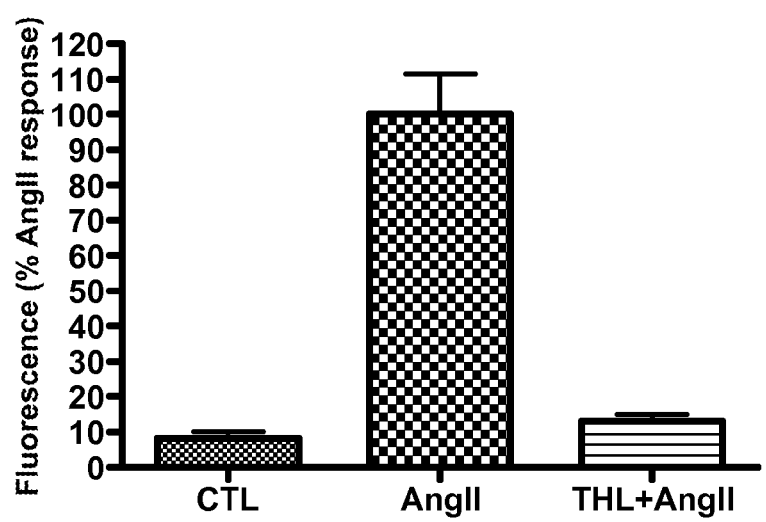
FIG. 7. High through-put screening assay. 24 h after plating, the cells were starved for 2 hours, then incubated with vehicle (DMSO) or with THL (1 μM) for 2 hours, then stimulated with Ang II (10 nM) for 3 minutes. The cells were processed for infrared detection of pERK.

Using the same conditions of inhibition of 2-AG production with THL, the associated receptor was stimulated with a constant concentration of agonist, and stimulated $CB_1R$ by concomitant treatment with increasing doses of 2-AG. A concentration-dependent 2-AG-mediated ERK1/2 phosphorylation was obtained. See FIGS. 6 and 7.

These data indicate that the receptor complex system can be used to screen for inhibitor of DAG lipase involved in the production of 2-AG: In basal conditions (in the absence of inhibition), the concentration of 2-AG is sufficient to allow ERK1/2 phosphorylation after stimulation of the associated receptor. In the case of inhibition of the DAG lipase, the absence of 2-AG prevents ERK1/2 phosphorylation induced by treatment with the ligand of the associated receptor. The same experiments were conducted as described above in 96-well plates. Similar results were obtained, indicating that this method can be used for screening of inhibitors of DAG lipase in a high-throughput scale.

For high-throughput screening, test concentrations of compounds may be between 10 and 100 mM. A cut-off of 100 mM may be used in selecting compounds active in the primary screen and counter-screening assays. First, the compounds are tested to determine if they can inhibit the activity of DAGL in the cell based assay described above using a compound concentration of 10 mM. A screening compound is selected for further testing as a DAGL inhibitor if it mediates at least a 70% or more decrease in Ang II-mediated ERK phosphorylation compared to the positive control. In all assays, THL is used as a positive control. Libraries of small molecules and drug-like pharmacophores may be used ERK phosphorylation is determined by Western blot using an antibody specific for phosphorylated ERK.

This DAGL-inhibitor screen is specific for $CB_1R$ activation, it is sensitive and is based on a simple assay (ERK1/2 phosphorylation) that can be easily adapted to high throughput. In addition, it does not involve measurement of lipid levels.

DISCUSSION

Preventing the expression or activation of $CB_1Rs$ attenuates the development of fibrosis[2]. Here a novel mechanism is described for the pivotal role of $CB_1R$ in liver disease, involving the formation of fibrosis-specific receptor heteromers consisting of upregulated $CB_1R$ with resident fibrogenic G protein coupled receptors (GPCRs) in activated HSCs. Specifically, there is enhanced association of $CB_1R$ with angiotensin II receptor (AT1R) and adenosine 2a receptor (A2aR) in activated HSCs and in liver from $CCl_4$ treated mice and cirrhotic human patient; within these complexes, AT1R and A2aR activity-mediated mitogenic signaling events that lead to profibrogenic effects are completely under the control of $CB_1R$ activity. Disrupting $CB_1R$ expression or activity leads to a dramatic decrease in angiotensin II-mediated fibrogenic signaling, demonstrating that $CB_1R$ controls AT1R signaling in activated HSCs. Similarly, association of $CB_1R$ with the adenosine 2a receptor (A2aR), another receptor involved in fibrosis 3 also leads to the control of adenosine signaling by $CB_1R$ and profibrogenic gene expression by $CB_1R$ in activated HSCs and in an experimental model of liver fibrosis. Taken together, these results demonstrate a general mechanism of signal hijacking by $CB_1R$ in activated HSCs and demonstrate the generation of context-dependent GPCR heteromers that occur only in a pathological state, which in turn leads to modification of signaling that contribute to the disease. Furthermore, the data herein define these receptor heteromers ($CB_1R$-AT1R and $CB_1R$-A2aR) as disease-specific drug targets for the treatment of liver fibrosis.

In this study, a mechanism was identified for the contribution of $CB_1R$ activity in liver fibrosis, through heteromerization with other GPCRs. Upregulated $CB_1R$ in activated HSCs forms complexes with AT1R and A2aR and this leads to a shift in G protein coupling and increased signaling, which ultimately results in enhancing the profibrogenic activity of these associating receptors.

The role of $CB_1R$ in liver disease is poorly understood. The finding herein, that $CB_1R$ uses other receptors to amplify their profibrogenic signaling sheds light on one mechanism by which $CB_1R$ regulates liver fibrosis. This, together with the possibility of auto and paracrine transactivation of $CB_1R$ by AT1R[11, 12] demonstrates a loop of amplification of cannabinoid/angiotensin and cannabinoid/adenosine signaling by several mechanisms converging towards upregulation of profibrogenic stimulation through the endocannabinoid system.

Another important finding in this study is that the basal $CB_1R$ activity is sufficient to enhance AT1R and A2aR responses. This demonstrates that low or no basal activity of $CB_1R$ can decrease the fibrogenic potential of Ang II and adenosine, underscoring a particularly important role for the endocannabinoid tone in the maintenance of fibrosis. Hence, inhibiting the enzymes involved in endocannabinoid production represents novel therapy for the treatment of liver fibrosis.

Abnormal production of 2-AG is a hallmark of a number of diseases, including liver fibrosis. Blocking the activation of the cannabinoid system by using cannabinoid receptor antagonists validates the cannabinoid system as an outstanding drug target. Because blocking of $CB_1R$ alone leads to adverse CNS effects, an alternative strategy to block the activation of the cannabinoid system was identified herein; namely, a screening method to identify inhibitors of the production of the abnormally high levels of endocannabinoid ligands. The few inhibitors of this pathway that have been identified are not orally active, limiting their use as pharmaceutically-acceptable drugs. Prior to this invention, there was no method suitable for the high throughput screening (HTS) of DAGL inhibitors. This is due to the lipidic nature of the substrates/products of DAGL that requires labor-intensive methods of analysis. The two main assays to measure DAGL activity currently are (i) measuring the conversion of sn-1-[3H]oleoyl-2-arachidonoylglycerol to [3H]oleic acid and 2-AG using thin layer chromatography; and (ii) measuring endocannabinoid levels by liquid chromatography coupled to mass spectrometry.

In summary, a novel, fast cell-based assay that measures endocannabinoid-mediated cell signaling is described. This assay takes advantage of the finding that CB1R heteromerization mediates changes in signaling. This assay is useful to screen for and identify DAGL inhibitors, which are valuable therapeutic tools for the treatment of liver diseases, such as cirrhosis and alcoholic and non-alcoholic fibrosis, obesity, metabolic disease.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

LITERATURE CITED

1. Friedman, S. L. Hepatic stellate cells: protean, multifunctional, and enigmatic cells of the liver. Physiol Rev 88, 125-72 (2008).
2. Teixeira-Clerc, F. et al. CB1 cannabinoid receptor antagonism: a new strategy for the treatment of liver fibrosis. Nat Med 12, 671-6 (2006).
3. Chan, E. S. et al. Adenosine A(2A) receptors play a role in the pathogenesis of hepatic cirrhosis. Br J Pharmacol 148, 1144-55 (2006).
4. Britton, R. S. & Bacon, B. R. Intracellular signaling pathways in stellate cell activation. Alcohol Clin Exp Res 23, 922-5 (1999).
5. Yoshiji, H., Kuriyama, S. & Fukui, H. Blockade of renin-angiotensin system in antifibrotic therapy. J Gastroenterol Hepatol 22 Suppl 1, S93-5 (2007).
6. Rozenfeld, R. & Devi, L. A. Regulation of CB1 cannabinoid receptor trafficking by the adaptor protein AP-3. Faseb J 22, 2311-22 (2008).
7. Vasquez, C. & Lewis, D. L. The CB1 cannabinoid receptor can sequester G-proteins, making them unavailable to couple to other receptors. J Neurosci 19, 9271-80 (1999).
8. Quitterer, U. & Lohse, M. J. Crosstalk between Galpha(i)- and Galpha(q)-coupled receptors is mediated by Gbetagamma exchange. Proc Natl Acad Sci USA 96, 10626-31 (1999).
9. Tohgo, A., Pierce, K. L., Choy, E. W., Lefkowitz, R. J. & Luttrell, L. M. beta-Arrestin scaffolding of the ERK cascade enhances cytosolic ERK activity but inhibits ERK-mediated transcription following angiotensin AT1a receptor stimulation. J Biol Chem 277, 9429-36 (2002).
10. Che, J., Chan, E. S. & Cronstein, B. N. Adenosine A2A receptor occupancy stimulates collagen expression by hepatic stellate cells via pathways involving protein kinase A, Src, and extracellular signal-regulated kinases 1/2 signaling cascade or p38 mitogen-activated protein kinase signaling pathway. Mol Pharmacol 72, 1626-36 (2007).
11. Turu, G. et al. The role of diacylglycerol lipase in constitutive and angiotensin AT1 receptor-stimulated cannabinoid CB1 receptor activity. J Biol Chem 282, 7753-7 (2007).
12. Turu, G. et al. Paracrine Transactivation of the CB1 Cannabinoid Receptor by AT1 Angiotensin and Other Gq/11 Protein-coupled Receptors. J Biol Chem (2009).
13. Hilairet, S., Bouaboula, M., Carriere, D., Le Fur, G. & Casellas, P. Hypersensitization of the Orexin 1 receptor by the CB1 receptor: evidence for cross-talk blocked by the specific CB1 antagonist, SR141716. J Biol Chem 278, 23731-7 (2003).
14. Kunos, G., Osei-Hyiaman, D., Liu, J., Godlewski, G. & Batkai, S. Endocannabinoids and the control of energy homeostasis. J Biol Chem 283, 33021-5 (2008).
15. AbdAlla, S., Lother, H., el Massiery, A. & Quitterer, U. Increased AT(1) receptor heteromers in preeclampsia mediate enhanced angiotensin II responsiveness. Nat Med 7, 1003-9 (2001).
16. Rozenfeld, R., Décaillot, F., IJzerman, A. P. & Devi, L. A. Heteromers of G protein-coupled receptors as novel and distinct drug targets. Drug Discovery Today: Therapeutic Strategies 3, 437-443 (2006).
17. Kunos, G., Osei-Hyiaman, D., Batkai, S., Sharkey, K. A. & Makriyannis, A. Should peripheral CB(1) cannabinoid receptors be selectively targeted for therapeutic gain? Trends Pharmacol Sci 30, 1-7 (2009).
(S1) Lieber C S, DeCarli L M. Liquid diet technique of ethanol administration: 1989 update. *Alcohol Alcohol* 1989; 24: 197-211
(S2) Cubero F J, Nieto N. Ethanol and arachidonic acid synergize to activate Kupffer cells and modulate the fibrogenic response via tumor necrosis factor alpha, reduced glutathione, and transforming growth factor beta-dependent mechanisms. *Hepatology.* 2008 December; 48(6):2027-39.
(S3) Urtasun R, Cubero F J, Vera M, Nieto N. Reactive nitrogen species switch on early extracellular matrix remodeling via induction of MMP1 and TNFalpha. *Gastroenterology.* 2009; 136: 1410-22
D1. Bisogno T. Endogenous cannabinoids: structure and metabolism. J Neuroendocrinol 2008; 20 Suppl 1:1-9.
D2. Zhang J, Chen C. Endocannabinoid 2-AG protects neurons by limiting cox-2 elevation. J Biol Chem 2008.
D3. Bab I, Ofek O, Tam J, Rehnelt J, Zimmer A. Endocannabinoids and the regulation of bone metabolism. J Neuroendocrinol 2008; 20 Suppl 1:69-74.
D4. Engeli S. Dysregulation of the endocannabinoid system in obesity. J Neuroendocrinol 2008; 20 Suppl 1:110-5.
D5. Caraceni P, Domenicali M, Bernardi M. The endocannabinoid system and liver diseases. J Neuroendocrinol 2008; 20 Suppl 1:47-52.
D6. Bisogno T, Howell F, Williams G, et al. Cloning of the first sn1-DAG lipases points to the spatial and temporal regulation of endocannabinoid signaling in the brain. J Cell Biol 2003; 163(3):463-8.
D7. Bisogno T, Cascio M G, Saha B, et al. Development of the first potent and specific inhibitors of endocannabinoid biosynthesis. Biochim Biophys Acta 2006; 1761(2):205-12.

What is claimed is:

1. An isolated monoclonal antibody which specifically binds to a type I cannabinoid receptor ($CB_1R$)/angiotensin II receptor (AT1R) heteromer.

2. A pharmaceutical composition comprising the monoclonal antibody of claim 1 and a pharmaceutically acceptable carrier or diluent.

* * * * *